United States Patent
Kreuger et al.

(10) Patent No.: US 11,427,851 B2
(45) Date of Patent: Aug. 30, 2022

(54) USE OF A FLUIDIC DEVICE

(71) Applicant: GRADIENTECH AB, Uppsala (SE)

(72) Inventors: Johan Kreuger, Uppsala (SE); Sara Thorslund, Uppsala (SE); Zhigang Wu, Uppsala (SE)

(73) Assignee: GRADIENTECH AB, Uppsala (SE)

( * ) Notice: Subject to any disclaimer, the term of this patent is extended or adjusted under 35 U.S.C. 154(b) by 507 days.

(21) Appl. No.: 16/660,064

(22) Filed: Oct. 22, 2019

(65) Prior Publication Data
US 2020/0048680 A1    Feb. 13, 2020

Related U.S. Application Data

(63) Continuation of application No. 14/903,032, filed as application No. PCT/SE2014/050883 on Jul. 10, 2014, now Pat. No. 10,487,349.

(30) Foreign Application Priority Data

Jul. 10, 2013  (SE) .................................... 1350861-9

(51) Int. Cl.
| | |
|---|---|
| *C12Q 1/18* | (2006.01) |
| *C12M 1/16* | (2006.01) |
| *C12Q 1/02* | (2006.01) |
| *C12M 3/06* | (2006.01) |
| *C12M 1/12* | (2006.01) |
| *C12M 1/00* | (2006.01) |

(Continued)

(52) U.S. Cl.
CPC ................. *C12Q 1/18* (2013.01); *C12M 1/16* (2013.01); *C12M 21/00* (2013.01); *C12M 23/16* (2013.01); *C12M 25/14* (2013.01); *C12M 41/46* (2013.01); *C12Q 1/02* (2013.01); *B01L 3/5027* (2013.01)

(58) Field of Classification Search
None
See application file for complete search history.

(56) References Cited

U.S. PATENT DOCUMENTS

| | | |
|---|---|---|
| 6,153,400 A | 11/2000 | Matsumura et al. |
| 8,216,526 B2 | 7/2012 | Locascio et al. |
| 2010/0035292 A1 | 2/2010 | Levhenko et al. |

(Continued)

FOREIGN PATENT DOCUMENTS

| | | |
|---|---|---|
| JP | 2011516079 A | 5/2011 |
| JP | 2011193758 A | 10/2011 |

(Continued)

OTHER PUBLICATIONS

Takagi, Rika, et al., A microfluidic microbial culture device for rapid determination of the minimum inhibitory concentration of antibiotics, Analyst, 138:1000-1003 (2013).

(Continued)

*Primary Examiner* — William H. Beisner
(74) *Attorney, Agent, or Firm* — Porter Wright Morris & Arthur LLP

(57) ABSTRACT

A fluidic device has a culture chamber configured to house a 3D culture matrix comprising a culture of microorganisms. A concentration gradient of a test substance is established over the 3D culture matrix by providing respective fluid flows at different end portions of the culture chamber and comprising different concentrations of the test substance. The response of the microorganisms to the test substance is determined based on the position of a border zone in the 3D culture matrix.

7 Claims, 10 Drawing Sheets

(51) Int. Cl.
  C12M 1/34 (2006.01)
  B01L 3/00 (2006.01)

(56) References Cited

U.S. PATENT DOCUMENTS

| | | |
|---|---|---|
| 2011/0159522 A1 | 6/2011 | Kamm et al. |
| 2011/0217771 A1 | 9/2011 | Thorslund et al. |
| 2012/0122831 A1 | 5/2012 | Sauer-Budge et al. |
| 2013/0171682 A1 | 7/2013 | Hung et al. |

FOREIGN PATENT DOCUMENTS

| | | |
|---|---|---|
| WO | 2009/061392 A1 | 5/2009 |
| WO | 2007/044888 A2 | 10/2009 |
| WO | 2010/018499 A1 | 2/2010 |
| WO | 2010/056186 A1 | 5/2010 |
| WO | 2011/044116 A2 | 4/2011 |
| WO | 2012/050981 A1 | 4/2012 |

OTHER PUBLICATIONS

Takagi, Rika, et al., Determination of the Minimum Inhibitory Concentration of Antibiotics against Bacteria using a Microfluidic Device, Chemical Sensors, vol. 28 Supplement A:46-48 (2012).
Hou, Zining, et al., Time lapse investigation of antibiotic susceptibility using a microfluidic linear gradient 3D culture device, Lab Chip, 14:3409-3418 (2014).
Boedicker et al., Detecting bacteria and determining their susceptibility to antibiotics by stochastic confinement in nanoliter droplets using plug-based microfluidics, Lab Chip, 8:1265-1272 (online Jul. 4, 2008).
Chen et al., Antimicrobial Susceptibility Testing Using High Surface-to-Volume Ratio Microchannels, Analytical Chemistry, 82:1012-1019 (online Jan. 7, 2010).
Choi et al., Rapid antibiotic susceptibility testing by tracking single cell growth in a microfluidic agarose channel system, Lab Chip, 13:280-287 (online Oct. 26, 2012).
Chung et al., Antibiotic susceptibility test based on the dielectroporetic behavior of elongated *Escherichia coli* with cephalexin treatment, Biomicrofluidics 5:021102-1-021102-6 (2011).
Churski et al., Rapid screening of antibiotic toxicity in an automated microdroplet system, Lab Chip 12:1629-1637 (online Feb. 8, 2012).
Cira et al., A self-loading microfluidic device for determining the minimum inhibitory concentration of antibiotics, Lab Chip, 12:1052-1059 (online Dec. 22, 2011).
Dittrich et al., Lab-on-a-Chip: microfluidics in drug discovery, Nature Reviews/Drug Discovery, 5:210-218 (Mar. 2006).
Eun et al., Encapsulating Bacteria in Agarose Microparticles Using Microfluidics for High-Throughput Cell Analysis and Isolations, ACS Chemical Biology, 6:260-266 (2011).
Haessler et al., An agarose-based microfluidic platform with a gradient buffer for 3D chemotaxis studies, Biomed Microdevices, 11:827-835 (2009).
Jorgensen et al., Antimicrobial Susceptibility Testing: A Review of General Principles and Contemporary Practices, Medical Microbiology, 49:1749-1755 (Dec. 1, 2009).
Kalashnikov et al., A microfluidic platform for rapid, stress-induced antibiotic susceptibility testing of *Staphylococcus aureus*, Lab Chip 12:4523-4532 (online Aug. 9, 2012).
Kim et al., In situ monitoring of antibiotic susceptibility of bacterial biofilms in a microfluidic device, Lab Chip, 10:3296-3299 (2010).
Kim et al., Targeting the leukocyte activation cascade: Getting to the site of inflammation using microfabricated assays, Lab Chip, 12:2255-2264 (online Mar. 8, 2012).
Kinnunen et al., Self-Assembled Magnetic Bead Biosensor for Measuring Bacterial Growth and Antimicrobial Susceptibility Testing, Small, 8(16):2477-2482 (online Jun. 5, 2012).
Nguyen et al., Biomimetic model to reconstitute angiogenic sprouting morphogenesis in vitro, PNAS, 110 (17):6712-6717 (Apr. 23, 2013).
Peitz et al., Single-cell bacteria growth monitoring by automated DEP-facilitated image analysis, Lab Chip, 10:2944-2951 (2010).
Sinn et al., Asynchronous magnetic bead rotation (AMBR) biosensor in microfluidic droplets for rapid bacterial growth and susceptibility measurements, Lab Chip, 11:2604-2611 (2011).
Frisk et al, A microfluidic device for parallel 3-D cell cultures in asymmetric environments, Electrophoresis, 28:4705-4712 (2007).
Search Report from corresponding European Application No. 14823735.7, dated Feb. 10, 2017.
Ryota Iino et al., A microfluidic device for simple and rapid evaluation of multidrug efflux pump inhibitors, Frontiers in Microbiology, 3:1-9 (published Feb. 8, 2012).
Hikida et al., Comparative Antibacterial Activity of Carbapenems Against P. Aeruginosa, The Japanese Journal of Antibiotics, vol. 56, No. 6, pp. 674-680 (Dec. 2003). English abstract at p. 680. Also see p. 3 of cited reference 3 (Official Action English Translation) for relevance.
Kachikukyozei ni okeru Kokinseibushitsu no Shiyoshishin, Norinsuisansho, 2009, pp. 49 to 58 (http://.maff.go.jp/j/heiei/hoken/saigai_hosyo/s_yoko/. See pp. 2-3 of cited reference 3 (Official Action English Translation) for relevance.
Official Action with English Translation dated Aug. 15, 2017 from corresponding Japanese Application 2016-525331.

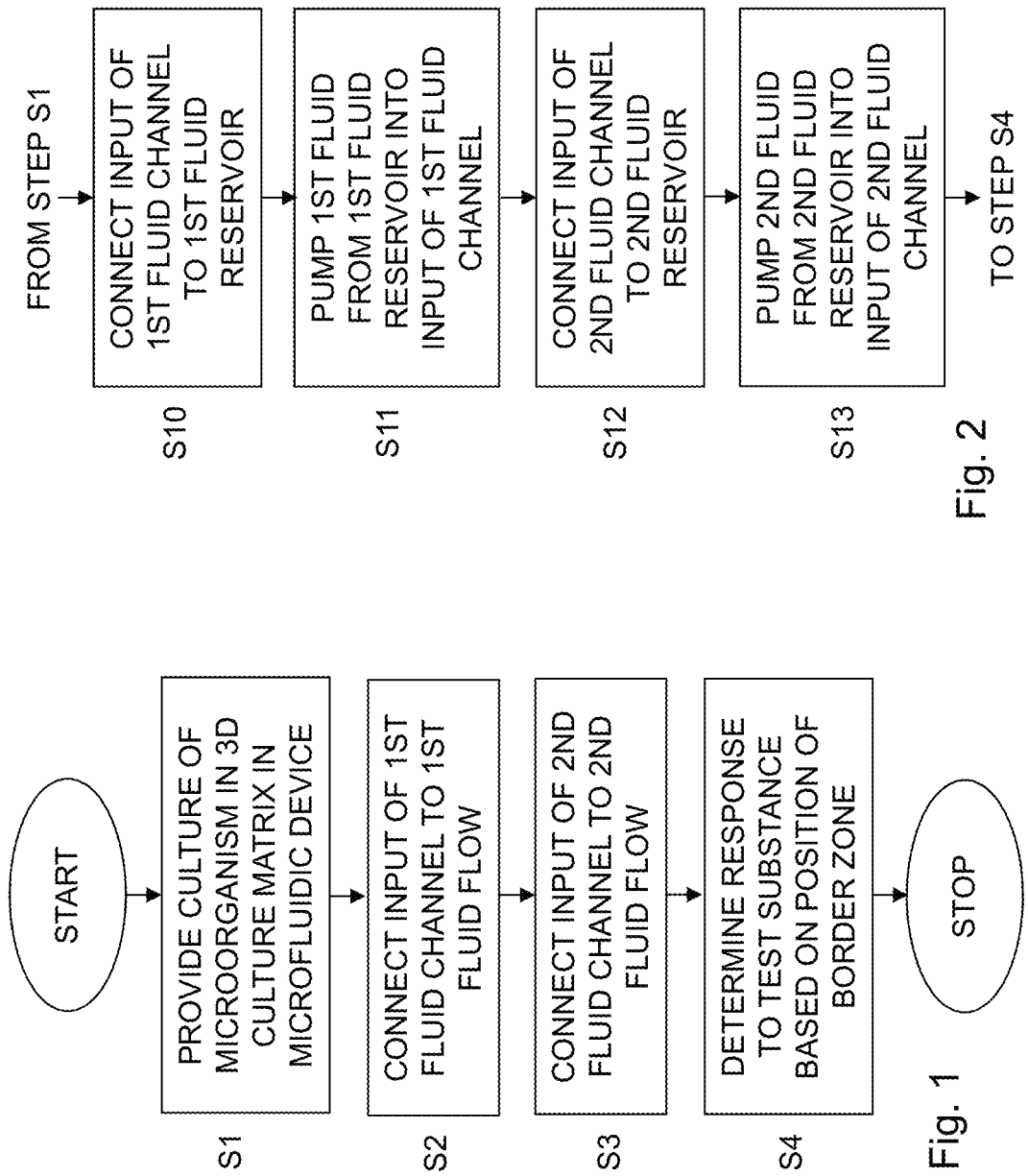

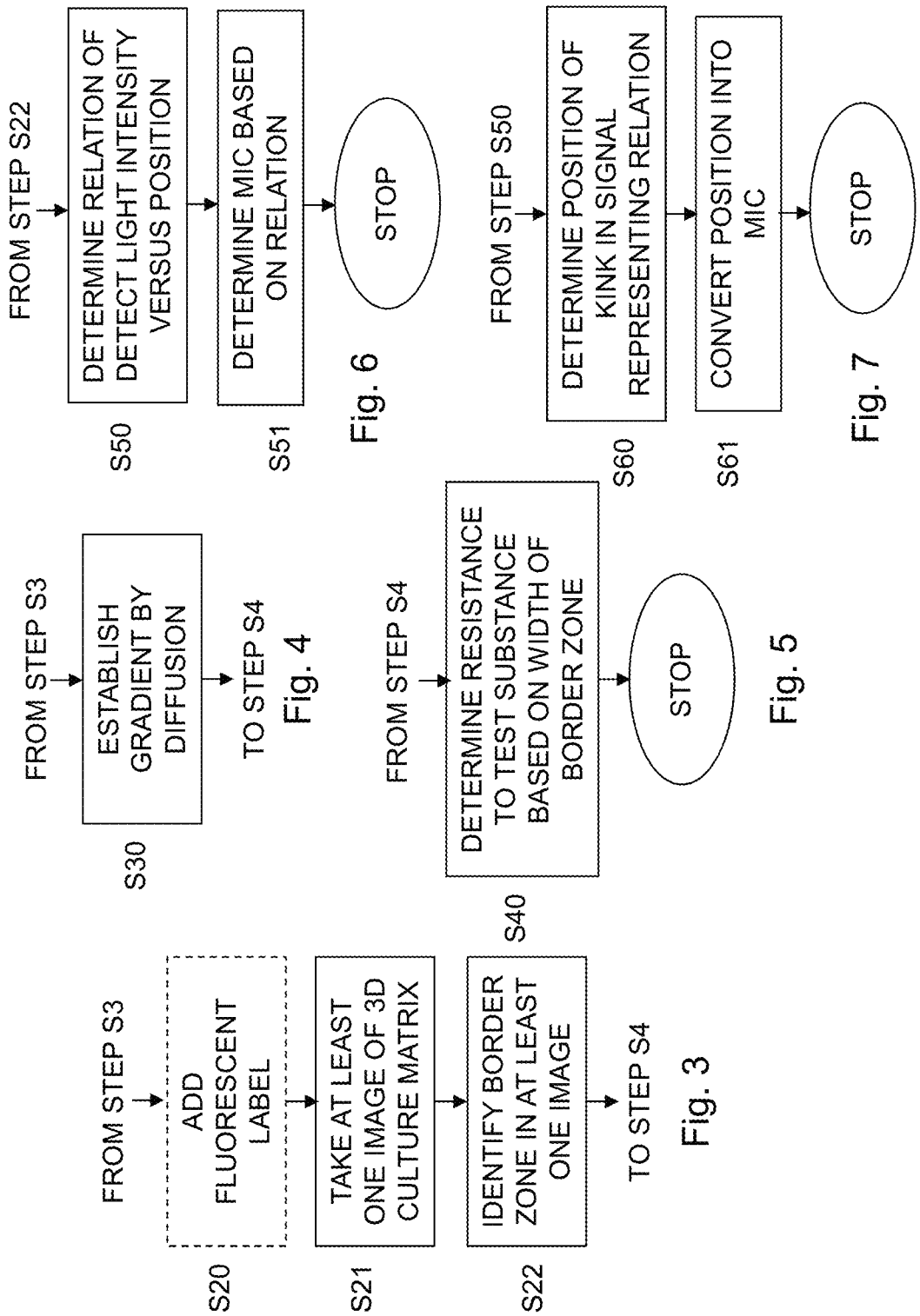

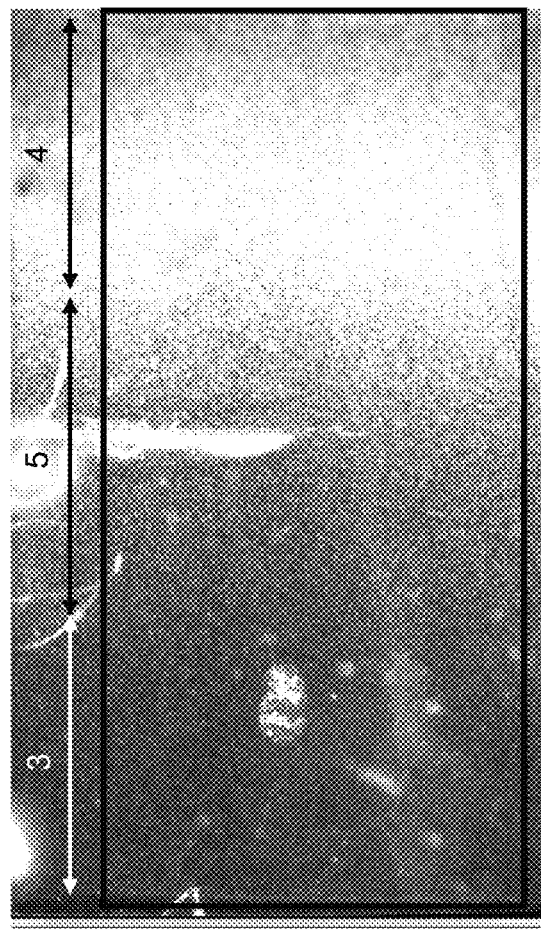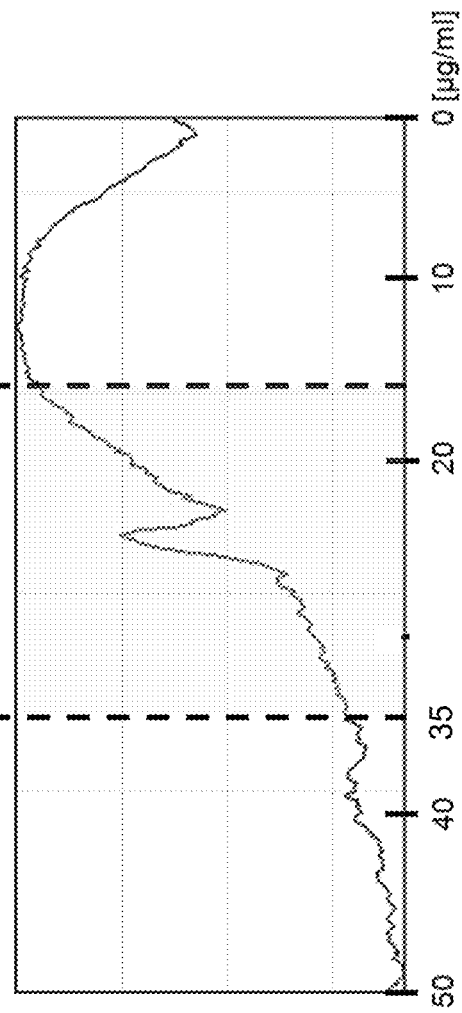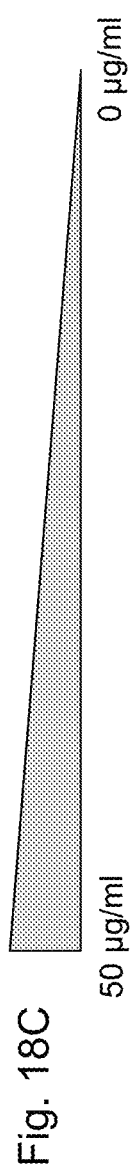
Fig. 18A
Fig. 18B
Fig. 18C

USE OF A FLUIDIC DEVICE

TECHNICAL FIELD

The embodiments generally relate to fluidic devices and in particular to the use of such fluidic devices in determining a response of microorganisms to test substances.

BACKGROUND

Antibiotic-resistant bacteria represent a growing global problem, as these bacteria cannot be killed or made to stop dividing by antibiotics. The generation time of bacteria can in many cases be very fast (around 20 minutes), and due to the short generation time and relative genetic instability of bacteria, the bacteria may quickly acquire resistance towards antibiotics. There is an increasing prevalence of antibiotic-resistant bacterial infections in the human population, and some of these bacteria have even become multi-resistant, sometimes meaning that there are no efficient antibiotics available to halt their growth. These multi-resistant bacteria are a serious public health problem as patients infected with such bacteria may die due to that their bacterial infections cannot be treated.

The traditional approaches for the identification and study of microorganisms, including but not limited to bacteria, fungi, parasites and viruses, and their resistance to antibiotics that kill or inhibit the growth of the microorganism, have mainly in the example of bacteria been limited to Luria broth (LB) agar plates. These LB agar plates have then been made to contain bactericidal and bacteriostatic antibiotics of defined concentrations. Such two-dimensional (2D) culture methods for antibiotic susceptibility testing (AST) and evaluation of the effects of antibiotics or other test substances on microorganisms have several limitations. For instance, these setups normally require that the microorganisms, e.g. bacteria, are cultured over night to allow for a clear result readout showing if a particular bacteria strain is resistant or not to a given antibiotic. In addition, generally only a single antibiotic concentration can be tested per LB agar plate.

Another prior art AST approach uses a so-called E-test. The E-test is basically an agar diffusion method and uses a rectangular strip impregnated with different concentrations of a test substance to be evaluated for its effect as an antibiotic. In a typical approach, bacteria are spread and grown in a 2D culture on top of an agar plate, where after the E-test strip is placed on top of the agar plate. The E-test strip releases the test substance by diffusion and the growth inhibitory effects of the released test substance are typically inspected after 24 hours of incubation. A limitation of this approach is, in addition to the very long incubation time, that readouts of the inhibitory concentration of the test substance is only possible in distinct digital steps and in the selected concentrations used in the E-test strip.

A further traditional AST approach uses a microtiter plate assay with different concentrations of a test substance in different wells. The microtiter plate with added bacteria is usually incubated overnight and the inhibitory effects on the bacteria are evaluated by measuring the optical turbidity in the different wells. This approach has basically the same shortcomings as when using E-test strips.

In order to reduce the AST time, microfluidic channel systems for rapid AST (RAST) have been developed. Such RAST approaches include droplet-based microfluidic channel systems in which bacteria are captured in a droplet that includes an antibiotic [1-3]. A limitation with the droplet-based system is that only a single antibiotic concentration can be tested. Other RAST approaches include using gas permeable polydimethylsiloxane (PDMS) microchannels [4], dielectrophoretic capturing of bacteria in microfluidic electrode structures [5-6], preloaded PDMS layers with antibiotics [7], covalently binding bacteria to microfluidic channels and subjecting them to mechanical shear stress [8], using asynchronous magnetic bead rotation (AMBR) biosensors [9] or tracking single cell growth in a microfluidic agarose channel system [10]. A major limitation of these various RAST approaches is that they can only test a single antibiotic concentration or a set of a few selected antibiotic concentrations.

It has further been proposed to use a microfluidic system for analysis of antibiotic susceptibility of bacterial biofilms [11]. Their microfluidic system, however, requires 24 hours of incubation and that the bacteria to be tested contain a plasmid able to express green fluorescent protein (GFP).

Hence, there is still a need for fast methods and systems for response testing of microorganism that do not have the disadvantages of the prior art.

SUMMARY

It is a general objective to enable efficient and fast determination of the response of microorganisms to test substances.

This and other objectives are met by embodiments as defined herein.

An aspect of the embodiments relates to a method of determining a response of a microorganism to a test substance. The method comprises providing a culture of the microorganism in a three-dimensional (3D) culture matrix arranged in a culture chamber of a fluidic device having a first fluid channel flanking a first end portion of the culture chamber and a second fluid channel flanking a second, different end portion of the culture chamber. The method also comprises connecting an input of the first fluid channel to a first fluid flow comprising the test substance at a first concentration. The method further comprises connecting an input of the second fluid channel to a second fluid flow lacking the test substance or comprising the test substance at a second concentration that is lower than the first concentration to from a concentration gradient of the test substance over at least a portion of the 3D culture matrix. The method additionally comprises determining a response of the microorganism to the test substance based on a position of any border zone in the 3D culture matrix relative to the first end portion and/or the second, different end portion. The border zone is between a first response zone in which the microorganism shows a first response to the test substance and a second response zone in which the microorganism shows a second, different response to the test substance.

Another aspect of the embodiments relates to a system for determining a response of a microorganism to a test substance. The system comprises a fluidic device comprising a culture chamber configured to house a culture of the microorganism in a 3D culture matrix. The fluidic device also comprises a first fluid channel flanking a first end portion of the culture chamber and a second fluid channel flanking a second, different end portion of the culture chamber. The system also comprises a first fluid reservoir comprising a first fluid comprising the test substance at a first concentration. The first fluid reservoir is configured to be connected to an input of the first fluid channel. The system further comprises a second fluid reservoir comprising a second fluid lacking the test substance or comprising the test substance at a second concentration that is lower than the first concentration. The second fluid reservoir is configured to be connected to an input of the second fluid channel to form a concentration gradient of the test substance over at least a portion of the 3D culture matrix. The system additionally comprises a computer-based system configured to take at least one image of the 3D culture matrix and process the at least one image to identify a position, relative to the first end portion and/or second end, different portion, of any border zone in the 3D culture matrix. The border zone is between a first response zone in which the microorganism shows a first response to the test substance and a second response zone in which the microorganism shows a second, different response to the test substance. The computer-based system is also configured to determine a response of the microorganism to the test substance based on the position of the border zone.

A further aspect of the embodiments relates to use of a fluidic device to determine a response of a microorganism to a test substance. The fluidic device comprises a culture chamber configured to house a culture of the microorganism in a 3D culture matrix. The fluidic device also comprises a first fluid channel flanking a first end portion of the culture chamber and configured to carry a first fluid flow comprising the test substance at a first concentration. The fluidic device further comprises a second fluid channel flanking a second, different end portion of the culture chamber and configured to carry a second fluid lacking the test substance or comprising the test substance at a second concentration that is lower than the first concentration to form a concentration gradient of the test substance over at least a portion of the 3D culture matrix. The use comprises determining the response of the microorganism to the test substance based on a position of any border zone in the 3D culture matrix relative to the first end portion and/or the second, different end portion. The border zone is between a first response zone in which the microorganism shows a first response to the test substance and a second response zone in which the microorganism shows a second, different response to the test substance.

The aspects of the embodiments enable a very quick and efficient determination of the response of microorganisms to various test substances. The response of microorganisms to a continuous range of concentrations can be tested according to the embodiments.

BRIEF DESCRIPTION OF THE DRAWINGS

The embodiments, together with further objects and advantages thereof, may best be understood by making reference to the following description taken together with the accompanying drawings, in which:

FIG. 1 is a flow diagram illustrating a method of determining a response of a microorganism to a test substance according to an embodiment;

FIG. 2 is a flow diagram illustrating an embodiment of the connecting steps in FIG. 1;

FIG. 3 is a flow diagram illustrating additional, optional steps of the method in FIG. 1 according to an embodiment;

FIG. 4 is a flow diagram illustrating an additional, optional step of the method in FIG. 1 according to an embodiment;

FIG. 5 is a flow diagram illustrating an additional, optional step of the method in FIG. 1 according to an embodiment;

FIG. 6 is a flow diagram illustrating additional, optional steps of the method in FIG. 3 according to an embodiment;

FIG. 7 is a flow diagram illustrating an embodiment of the determining MIC step in FIG. 6;

FIG. 18A illustrates an image taken of a 3D culture matrix following formation of a linear gradient of spectinomycin (50-0 µg/ml left to right) through the 3D matrix with *E. coli* K12 MG1655 (the black box indicates the selected area for intensity measurements);

FIG. 18B illustrates an intensity profile of the selected area in FIG. 18A;

FIG. 18C schematically illustrates the linear gradient of spectinomycin (50-0 µg/ml) through the 3D culture matrix of FIG. 18A;

DETAILED DESCRIPTION

Figure 8:
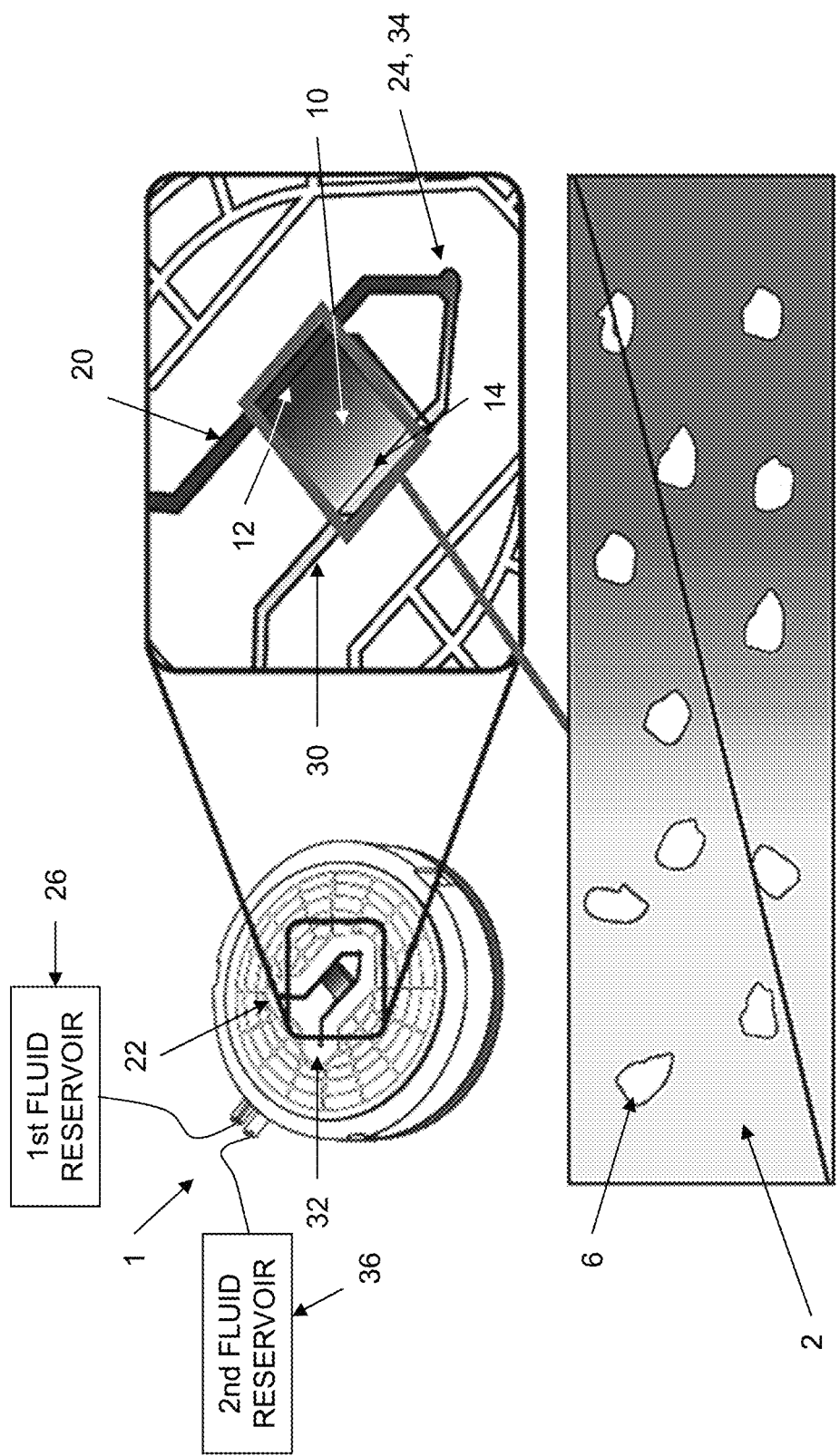
FIG. 8 is a schematic overview of a microfluidic device and a 3D culture matrix with microorganisms according to an embodiment.

Throughout the drawings, the same reference numbers are used for similar or corresponding elements.

The present embodiments generally relate to fluidic devices and in particular to the use of such fluidic devices in determining responses of microorganisms to test substances.

It has been concluded that fluidic devices, such as microfluidic devices, can be designed to be particularly suitable to monitor or determine the response of microorganisms to various test substances. In more detail, such fluidic devices, having a culture chamber with a three-dimensional (3D) culture matrix containing a culture of the relevant microorganisms, provide an efficient tool to quickly determine the response of the microorganisms to the test substance or indeed to any combination of multiple test substances.

Such fluidic devices have key features that make them a very efficient tool. Firstly, a steady-state gradient of the relevant test substance can quickly and accurately be established over at least a portion of the 3D culture matrix. This means that a continuous range of test substance concentrations is established from a high concentration at one of the end portions or sides of the 3D culture matrix down to a low or zero concentration at another end portion or side of the 3D culture matrix. Hence, a continuous range of concentrations of the test substance can be tested with a single fluidic device. This is in clear contrast to prior art techniques where one or at most a few predefined concentrations but not any continuous range of concentrations can be tested. Accordingly, a more exact determination of, for instance, minimum inhibitory concentration of an antibiotic can be made.

Secondly, the microorganisms are cultured in a 3D culture matrix. Accordingly, the microorganisms are allowed to grow in three dimensions. This in turn provides a much more significant difference between areas of the 3D culture matrix where viable and growing microorganisms are present and areas with cell death or low growth. Accordingly, the embodiments provide an enhanced signal-to-noise ratio. Hence, it is much easier to differentiate between different areas or zones in the 3D culture matrix as compared to growing microorganisms as a biofilm on a two-dimensional (2D) surface where fewer microorganisms can be grown and, thus, lower detection signals are generated.

A gradient of the test substance can quickly be established over at least a portion of the 3D culture matrix. This together with the possibility of microorganism growth in three dimensions enables reading the response of the microorganisms to the test substance in a very short time, generally within one or at most a few hours. This should be compared to several of the prior art techniques, typically requiring incubation overnight.

The fluidic device is advantageously provided as a small-scale device, i.e. a microfluidic device or even a nanofluidic device. Accordingly, small amounts of the test substance and the microorganisms are needed to successfully run a test.

Determining or monitoring the response of the microorganisms to the test substance can be made using common microscopy or indeed even by the human eye. Hence, generally no complex and specifically designed detection equipment is needed in order to determine the response of the microorganisms to the test substance.

The embodiments use a fluidic device in the monitoring and determination of the response of microorganisms to various test substances. A fluidic device, also referred herein as a fluidic culture device, implies that fluid flows are present in channels of the fluidic device in order to transport the test substance to a culture chamber and thereby further into the 3D culture matrix present in the culture chamber.

The fluidic device is advantageously a so-called microfluidic device or microfluidic culture device. Microfluidic implies that the fluid channels of the microfluidic device are microsized channels. Generally, for such fluid channels with dimensions in the sub-micrometer range, the expression nanofluidics is often used. Hence, the fluidic device of the embodiments could also be such a nanofluidic device or nanofluidic culture device.

The fluid channels of the fluidic culture device are configured to carry a respective fluid flow. The fluid flow is preferably a liquid flow of a liquid in the fluid channel. However, it is also possible to have a flow of gas in the fluid channel or indeed a flow of fluidized solids or particles. Also a liquid flow with dissolved gas therein can be used according to the embodiments.

In a general embodiment, the fluidic device 1, see FIG. 8, comprises a culture chamber 10 configured to house a culture of a microorganism 6 in a 3D culture matrix 2. The fluidic device 1 also comprises a first fluid channel 20 flanking a first end portion or side 12 of the culture chamber 10 and a second fluid channel flanking a second, different end portion or side 14 of the culture chamber 10. The first fluid channel 20 is then configured to carry a first fluid flow comprising a test substance at a first concentration. The second fluid channel 30 is correspondingly configured to carry a second fluid flow lacking the test substance or comprising the test substance at a second concentration that is lower than the first concentration to form a concentration gradient of the test substance over at least a portion of the 3D culture matrix 2.

In order to form a concentration gradient of the test substance over at least a portion of the 3D culture matrix 2 the two fluid flows should comprise the test substance at different concentrations. Herein, the first fluid flow is defined as the fluid flow that comprises the test substance at the highest concentration. This means that the second fluid flow either lacks the test substance or comprises the test substance at a different, i.e. lower, concentration as compared to the first fluid flow.

The two fluid flows preferably have the same ingredient(s) or constituent(s) with the exception of one or more test substances to be tested. Hence, if the fluid flows are liquid flows the first and second fluid flows preferably comprise the same liquid or liquid mixture to which the test substance is added at the selected first concentration or the selected first and second concentrations. Correspondingly, if the two fluid flows are gas flows the first and second fluid flows preferably comprise the same gas or gas mixture to which the test substance is added at the selected concentration(s).

The embodiments can generally use any fluidic device having a culture chamber configured to house a 3D culture matrix and being flanked at different end portions with respective fluid channels. There are several such fluidic channels available in the art. For instance, a microfluidic device that works excellent according to the embodiments is marketed as CELLDIRECTOR® Ruby by Gradientech AB (Uppsala, Sweden). Fluidic devices that can be used according to the embodiments are also disclosed in, for instance, the following references [12-17, 19], the teachings of which with regard to microfluidic devices are hereby incorporated by reference.

Figure 20:
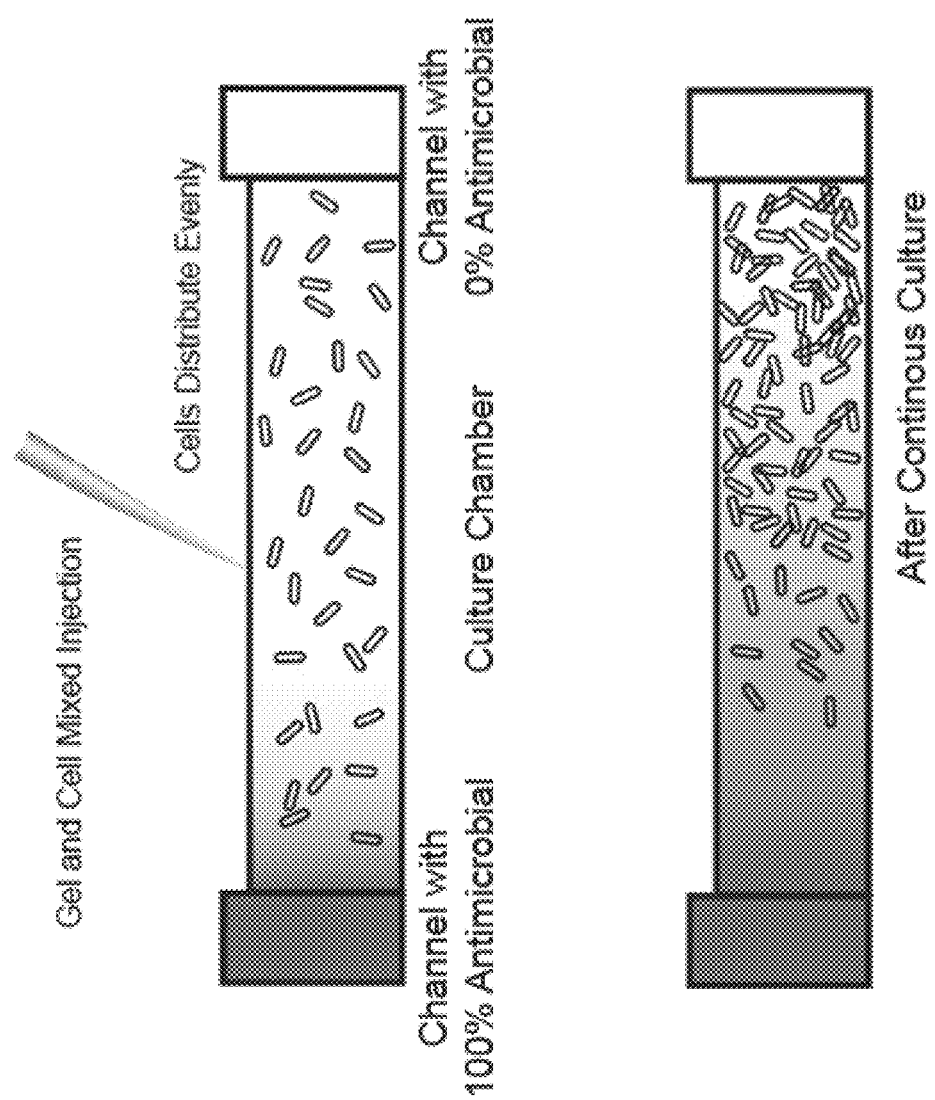
FIG. 20 schematically illustrates the results of culturing cells in a microfluidic device with a stable and continues gradient of an antimicrobial.

FIG. 20 schematically illustrates injecting a gel and cell mixture into a culture chamber of a microfluidic device. The cells are initially evenly distributed in the formed 3D culture matrix. In the illustrative example, a stable and continuous gradient was established by providing a first fluid flow comprising an antimicrobial and a second fluid flow lacking the antimicrobial. The gradient is thereby established over the culture chamber and the 3D culture matrix. The lower figure illustrates the result of culturing the cells in the 3D culture matrix and exposing them to the gradient of the antimicrobial.

FIG. 1 is a flow diagram of a method of determining a response of a microorganism to a test substance according to an embodiment. The method comprises providing, in step S1, a culture of the microorganism in a 3D culture matrix arranged in a culture chamber of a fluidic device. This fluidic device has a first fluid channel flanking a first end portion or side of the culture chamber and a second fluid channel flanking a second, different end portion or side of the culture chamber. A next step S2 comprises connecting an input of the first fluid channel to a first fluid flow comprising the test substance at a first concentration. Step S3 correspondingly comprises connecting an input of the second fluid channel to a second fluid flow lacking the test substance or comprising the test substance at a second concentration that is lower than the first concentration. Consequently, a concentration gradient of the test substance is thereby formed over at least a portion of the 3D culture matrix. A next step S4 determines a response of the microorganism to the test substance based on a position of any border zone in the 3D culture matrix relative to the first end portion or side and/or relative to the second, different end portion or side. This border zone is present between a first response zone in which the microorganism shows a first response to the test substance and a second response zone in which the microorganism shows a second, different response to the test substance.

The two steps S2 and S3 can be performed serially in any order, i.e. step S2 prior to or after step S3. Alternatively, the two steps S2 and S3 are performed at least partly in parallel.

The responses of the microorganisms in the 3D culture matrix to the test substance imply that at least three clearly visible zones will generally be present. These zones include the first response zone in which the microorganisms show a first response to the test substance. This first response zone is the zone closest to the first end portion or side and the first fluid channel. Hence, the first response zone corresponds to the portion of the 3D culture matrix exposed to a higher concentration of the test substance. The zones also include the second response zone in which the microorganisms show a second response to the test substance and where this second response is different from the first response. The second response zone is the zone closest to the second end portion or side and the second fluid channel. Hence, the second response zone corresponds to the portion of the 3D culture matrix exposed to a lower concentration of the test substance.

Figure 17A:
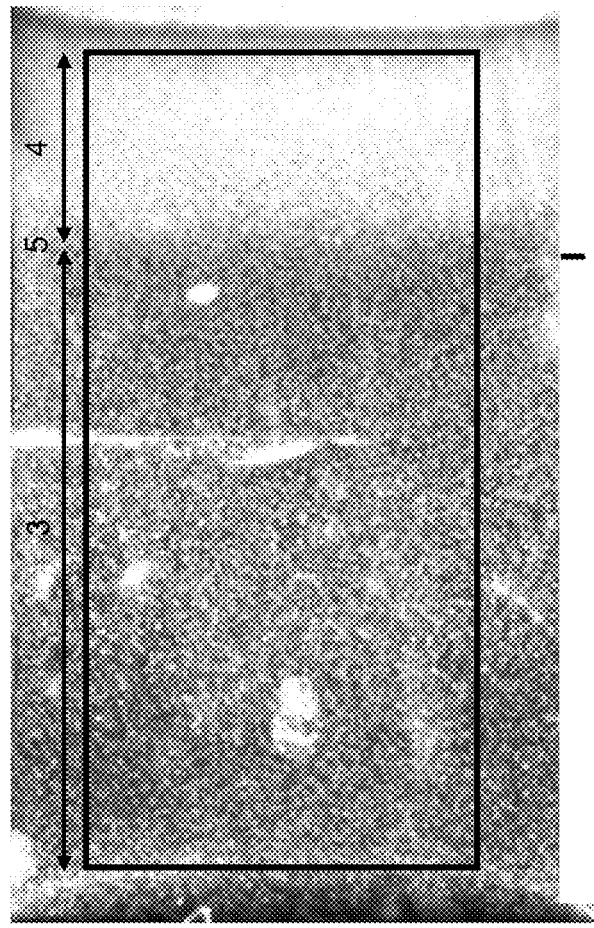
FIG. 17A illustrates an image taken of a 3D culture matrix following formation of a linear gradient of ampicillin (20-0 µg/ml left to right) through the 3D culture matrix with *E. coli* K12 MG1655 (the black box indicates the selected area for intensity measurements)

The border zone then constitutes the portion of the 3D culture matrix present in between the first response zone and the second response zone. This border zone 5 could be very thin, basically a boundary or border between the first response zone 3 and the second response zone 4 as shown in FIG. 17A. Alternatively, the border zone 5 has a wider extension in the 3D culture matrix between the first and second end portions or sides as shown in FIG. 18A.

The border zone thereby constitutes the portion of the 3D culture matrix where the local concentration of the test substance achieves a shift or change in response to the test substance from the first response in the first response zone to the second response in the second response zone.

For instance, if the test substance is an antibiotic or another bactericide or bacteriostat the second response zone, in which the microorganisms, here represented by bacteria, are exposed to a comparatively low concentration of the test substance, could be the portion of the 3D culture matrix with viable and growing bacteria. The first response zone is then preferably the portion of the 3D culture matrix where there is substantially no viable or growing bacteria, hence the first response zone is characterized by a relative lack of bacteria (due to cell death or no cell growth). The border zone then constitutes the border or portion between the growing/viable portion and the non-growing/cell death portion.

FIG. 17A clearly shows a second response zone 4 with growing bacteria (seen as white signal in the figure). In this portion of the 3D culture matrix the concentration of the test substance, here ampicillin, is too low to prevent cell growth or induce cell death among the *Escherichia coli* K12 MG1655 bacteria. In the first response zone 3 the concentration of ampicillin is, however, sufficiently high to prevent cell growth or induce cell death. Hence, substantially no *E. coli* K12 MG1655 are seen in this portion of the 3D culture matrix. In the shown experiment the border zone 5 is basically a clear border or boundary defining the minimum inhibitory concentration (MIC) of ampicillin for this particular *E. coli* strain.

In FIG. 18A the situation is somewhat different with a broader border zone 5 in between the second response zone 4 with viable and growing *E. coli* K12 MG1655 and the first response zone 3 where the concentration of spectinomycin as test substance was sufficiently high to kill the bacteria or at least prevent growth of any bacteria. In this experiment, some of the *E. coli* K12 MG1655 show resistance to the antibiotic spectinomycin as shown by some viable and growing bacteria in the border zone 5. The amount of bacteria in this border zone 5 is, however, significantly lower and different from the amount of bacteria in the second response zone 4 as clearly shown in FIG. 18A.

In a corresponding setting where the motility response of microorganisms is to be tested the second response zone could be the portion of the 3D culture matrix with low or no motility of the microorganisms (if the test substance induced motility among otherwise rather immobile microorganisms) or with high motility of the microorganisms (if the microorganisms are motile and the test substance inhibits this motility). The first response zone could then be the portion of the 3D culture matrix with sufficiently high concentration of the test substance to induce motility among the microorganisms or inhibit motility of the microorganisms. The border zone is then the portion of the 3D culture matrix between the first and second response zones and is characterized by the switch or change in motility from the immobile/low motility portion on one side of the border zone to the motile/high motility portion on the other side of the border zone. The border zone could then be a clear border or boundary similar to FIG. 17A or a wider portion with some intermediate motility of the microorganisms.

Motility and cell death are merely examples of responses of microorganisms that can be monitored and determined according to the embodiments. Other, non-limiting, examples include cell growth, proliferation, response behaviour to various forms of induced stress, matrix adhesion, mutability, etc.

The microorganisms, the response of which is to be determined, can be any microorganisms that can be grown and cultured in a 3D culture matrix of the fluidic device. Non-limiting examples of such microorganisms include bacteria, fungi, parasites, viruses and also cells, such as human cells or other mammalian cells. A single species or strain of the microorganisms could be tested and thereby cultured in the 3D culture matrix. Alternatively, a combined response of multiple, i.e. at least two, microorganisms could be determined. In such an approach, multiple different microorganisms are co-cultured in the 3D culture matrix.

The 3D culture matrix can be made of any material that is suitable as a culture matrix for the relevant microorganism(s). Such a material can be selected among traditionally used materials for cell cultures. Preferred but non-limiting examples of materials include agar; agarose; collagen I; extracellular matrix (ECM) gels, such as MATRIGEL™; hydrogels, such as a mixture of phenylalanine (Phe) dipeptide formed by solid-phase synthesis with a fluorenylmethoxycarbonyl (Fmoc) protector group on the N-terminus, and Fmoc-protected lysine (Lys) or solely phenylalanine.

In a particular embodiment, the microorganisms are of one bacterium strain and the test substance is an antibiotic and the MIC of the antibiotic is determined by the fluidic device.

The response of the microorganisms in the 3D culture matrix to the test substance is determined in step S4 of FIG. 1 based on the position of the border zone relative to the first and/or second end portion or side of the culture chamber. This position of the border zone relative to the end portions or sides of the culture chamber correlates to a concentration or at least a concentration range of the test substance. Hence, the position of the border zone or the distance between the border zone and the first end portion or side and/or the distance between the border zone and the second, different end portion or side corresponds to a concentration or concentration range of the test substance. Accordingly, it is possible to accurately determine the concentration or concentration range at which the response of the microorganisms changes or switches from the first response in the first response zone to the second response in the second response zone.

This further means that the position of the border zone can thereby be transformed or converted into, for instance, a MIC of an antibiotic, a motility inhibitory/promoting concentration of a test substance that inhibits/induces motility of the microorganisms, an adhesion inhibitory/promoting concentration of a test substance that inhibits/induces matrix adhesion of the microorganisms, etc.

In a particular embodiment, step S4 comprises determining the response of the microorganism to the test substance based on the position, relative to the first end portion and/or second, different end portion, of the border zone in the 3D culture matrix and based on the width of the border zone. Hence, in this particular embodiment, not only the position of the border zone, i.e. the distance between border zone and the first and/or second end portion of the culture chamber, but also the width of the border zone is used when determining the response. For instance, if the width of the border zone is substantially zero (see FIG. 17A), i.e. basically a boundary or border between the first and second response zones, the change in response of the microorganisms occurs at a specific concentration of the test substance. However, if the border zone has a non-zero width (see FIG. 18A) the change in response of the microorganisms occurs at a concentration range corresponding to the respective ends of the border zone.

A border zone with a non-zero width may further provide information with regard to any resistance of the microorganisms to the test substance. Hence, an extended border zone may imply that a resistance to the test substance is present in some of the microorganisms, for instance since they are able to grow at concentrations of the test substance which otherwise kill or prevent growth to non-resistant microorganisms. This means that the width of the border zone can be used in order to determine or detect any resistance at a given time of the microorganisms to the test substance.

In fact, it is actually possible with the fluidic device and method of the embodiments to detect any mutation in the microorganisms that induced resistance to the test substance or indeed caused loss of resistance to the test substance. Thus, the width of the border zone over time could be monitored when running the fluidic device with the culture of microorganisms in the 3D culture matrix and with the first and second fluid flows through the first and second fluid channels. An increase in the width of the border zone over time then typically implies gain of resistance to the test substance among at least some of the microorganisms. Correspondingly, a decrease in the width of the border zone typically implies loss of resistance to the test substance among microorganisms that previously showed resistance to the test substance.

Accordingly, in a particular embodiment it is preferred to use not only the position of the border zone but also its width when determining the response of the microorganisms to the test substance.

In more complex set-ups and arrangements of the fluidic device using multiple test substances and gradients, not only the width of the border zone or border zones may be of relevance. In these cases, also, or instead, the actual shape of the border zone(s) could be descriptive of the response of the microorganisms to the test substance(s). The shape of the border zone(s) could then encompass parameters such as area, curvature, width in different directions, etc. Hence, in a particular embodiment, the position of the border zone and the shape of the border zone are used when determining the response of the microorganisms to the test substance(s).

FIG. 2 is a flow diagram illustrating steps S2 and S3 in FIG. 1 according to a particular embodiment. This figure with be further described below with further reference to FIG. 8 and the fluidic device 1 shown therein. The method continues from step S1 in FIG. 1. A next step S10 comprises connecting the input 22 of the first fluid channel 20 to a first fluid reservoir 26 comprising a first fluid with the test substance at the first concentration. A next step S11 comprises pumping or otherwise providing the first fluid from the first fluid reservoir 26 into the input 22 of the first fluid channel 20 and out through an output 24 of the first fluid channel 20.

Step S12 comprises connecting the input 32 of the second fluid channel 30 to a second fluid reservoir 36 comprising a second fluid lacking the test substance or comprising the test substance at the second concentration. The following step S13 comprises pumping or otherwise providing the second fluid from the second fluid reservoir 36 into the input 32 of the second fluid channel 30 and out through an output 34 of the second fluid channel 30. The method then continues to step S4 of FIG. 1.

Hence, in a particular embodiment each fluid channel 20, 30 is connected to a fluid reservoir 26, 36 comprising the fluid to flow through the fluid channel 20, 30 and transport the test substance to the 3D culture matrix 2 in the culture chamber 10. The fluids can be drawn from the fluid reservoirs 26, 36 and into the fluid channels 20, 30 using any equipment (not shown) capable of establishing a flow of the fluids through the fluid channels 20, 30. Typically, fluid pumps or pushers are arranged in the fluid paths from the fluid reservoirs 26, 36 and the inputs 22, 32 of the fluid channels 20, 30 and/or connected to the output(s) 24, 34 of the fluid channels 20, 30. It may be possible use a single pump or pusher that operates on both fluid paths.

In FIG. 8 the fluid channels 20, 30 have a common output 24, 34. Hence, the first fluid channel 20 and the second fluid channel 30 merge at a point downstream of the culture chamber 10. In an alternative approach, each fluid channel 20, 30 has a respective output 24, 34.

The pumping of the fluids from the reservoirs 26, 36 into the inputs 22, 32 of the fluid channels 20, 30 is preferably performed throughout the usage or operation of the fluidic device 1 to determine the response. Hence, the pumping of the fluid is preferably performed at least until the response of the microorganisms 6 to the test substance has been determined.

The fluids present in the two fluid reservoirs 26, 36 are preferably the same fluid with the exception of the respective concentrations of the test substance(s).

Providing an even and non-fluctuating flow of the fluids through the fluid channels 20, 30 implies that a gradient of the test substance will be established over at least a portion of the 3D cell matrix 2. This means that when the fluid channels 20, 30 are connected to the fluid reservoirs 26, 36 and pumping of the fluids through the channels has just started no concentration gradient of the test substance has yet established over the 3D culture matrix 10. In clear contrast, the first end portion or side 12 of the culture chamber 10 is exposed to the first concentration of the test substance and the second end portion or side 14 of the culture chamber 20 is exposed to the second concentration of the test substance or is not exposed to the test substance at all. At this point substantially no test substance has diffused into the 3D culture matrix 2, which then typically has a zero concentration of the test substance. Over time the test substance is diffusing from the first fluid in the first fluid channel 20 into the 3D culture matrix 2. Eventually, a steady-state concentration gradient of the test substance is established over at least a portion of the 3D culture matrix 2 with the first end of the 3D culture matrix 2 facing the first fluid channel 20 having the first concentration of the test substance and the second end of the 3D culture matrix 2 facing the second fluid channel 20 having zero or the second concentration of the test substance.

In FIG. 2 a fluidic device 1 with two fluid channels 20, 30 have been assumed. If more than two fluid channels 20, 30 flank respective end portions of the culture chamber 10 then a respective connecting and pumping step is preferably performed for each such fluid channel.

In FIG. 2 the steps have been presented in a serial order. Steps S10 and S12 can be performed serially in any order or at least partly in parallel. The pumping of steps S11 and S13 are typically performed in parallel and throughout the whole usage or operation of the fluidic device 1.

Hence, in a particular embodiment the method comprises an additional step S30 as shown in FIG. 4. The method continues from step S3 of FIG. 1 or indeed from step S13 in FIG. 2. This additional step S30 comprises establishing a concentration gradient over at least a portion of the 3D culture matrix by diffusion of the test substance from the first fluid flow into the 3D culture matrix 2. This diffusion of the test substance is preferably achieved with substantially no flow of the first or second fluid through the 3D culture matrix.

Hence, the diffusion is from a so-called source fluid channel 20, which has a higher concentration of the test substance in the fluid relative the other fluid channel, denoted sink fluid channel 30. In a preferred embodiment, the flow rates of the fluids in the two fluid channels 20, 30 are preferably kept substantially similar since then no flow of the fluid is present through the 3D culture matrix 2 in the culture chamber 10. Substantially similar indicates that the two flow rates are preferably identical but can differ slightly due to inherent variations in the flow rate of the pumping systems. Thus, the difference in flow rate in the two fluid channels 20, 30 are preferably less than 10%, more preferably less than 5%, such as less than 2.5% and most preferably less than 1%.

If there is no net flow of the fluid over the 3D culture matrix 2 and the parts of the fluid channels 20, 30 adjacent a culture chamber 10 with a rectangular or quadratic bottom area, then the concentration gradient over the 3D culture matrix 2 will be linear.

The concentration gradient of the test substance can be established over the whole 3D culture matrix or over a portion of the 3D culture matrix depending on the positions of the fluid channels relative to the culture chamber and the shape of the culture chamber and the 3D culture matrix arranged therein.

In an embodiment, the respective concentrations of the test substance in the two fluid flows are fixed throughout the procedure. Hence, in such a case, the first concentration and the second concentration (if non-zero) are preferably fixed. In another embodiment, it is possible to change or adjust the concentration of the test substance in at least in one of the fluid flows during the procedure. Such a change could be in terms of one or more steps in concentration, i.e. switching from an initial concentration to a new concentration of the test substance. Alternatively, the change in concentration could be gradual and over time.

A change in concentrations could, for instance, be used if the initial concentrations of the test substance in the fluid flows did not result in any detectable effect. For instance, a too low concentration of an antibiotic in both fluid flows and thereby obtaining microorganism growth throughout the whole 3D culture matrix could be a case where it is appropriate to increase the concentration of the antibiotic in at least the first fluid channel.

A change in the concentration of the test substance in at least one of the fluid flows can also be used in various stress tests.

FIG. 3 is a flow diagram illustrating additional steps of the method according to various embodiments. In an embodiment, the method continues from step S3 of FIG. 1 (or from step S13 in FIG. 2 or step S30 in FIG. 4). A next step S21, in this embodiment, comprises taking at least one image or picture of the 3D culture matrix. The border zone is then identified in the at least one image in step S22. The method then continues to step S4 of FIG. 1, where the response of the microorganism to the test substance is determined based on the position of the border zone relative to the first and/or second end portion or side of the 3D culture matrix and where this position is identified in the at least one image.

Hence, one or more images are taken of the 3D culture matrix and the border zone is then identified in at least one of these images. The position of the border zone and optionally also the width and/or shape of the border zone can then be determined, either manually from the image, or by image processing using suitable equipment as is further disclosed herein.

In a particular embodiment, the at least one image of the 3D culture matrix is taken in step S21 using a bright-field microscope or using a phase-contrast microscope. In such a case, the position and optionally the width and/or shape of the border zone can be identified based on the detected light intensity in the at least one image. In an embodiment, step S22 therefore comprises processing the at least one image by a computer configured to identify the border zone based on detected light intensity in the at least one image.

Hence, in most embodiments there will be a clear visual difference between the first response zone and the second response in an image taken using a bright-field or phase-contrast microscope of the 3D culture matrix. As a consequence, the light intensity detected in the image can be used to manually, or using a computer with suitable image-processing program or software, identify the position and optionally the width and/or shape of the border zone in the image. This means that in most practical embodiments no staining or labelling of the microorganisms is needed.

It is, however, possible to have an additional, optional step S20, which comprises adding at least one fluorescent label to the 3D culture matrix. This fluorescent label is then configured to bind to the microorganism or to be taken up by the microorganism. In such a case, the at least one image of the 3D culture matrix is preferably taken using a fluorescent or confocal microscope in step S21. The border zone can then be identified in step S22 by processing the at least one image by a computer configured to identify the border zone based on detected fluorescence in the at least one image. Alternatively, manual inspection of the at least one image could be used to identify the border zone (position and optional width and/or shape) based on the fluorescence in the at least image.

In the above described embodiment, at least one fluorescent label has been added to the 3D culture matrix. In an alternative approach, the microorganisms could themselves express at least one substance, such as fluorescent substance, that could be detected in an image taken using a fluorescence or confocal microscope, or indeed any other imaging technique. Alternatively, the microorganisms can be made to express such a substance, for instance by transfection of an engineered expression vector that encodes such a substance. Hence, in such approaches the addition of the fluorescent label in step S20 could be omitted.

In a preferred embodiment, step S21 comprises taking at least one image of the 3D culture matrix at least after formation of a steady-state concentration gradient of the test substance over at least a portion of the 3D culture matrix. Hence, in a particular approach it is preferred to first establish the steady-state concentration gradient before determining the response of the microorganisms to the test substance. Thus, the at least one image to be taken and analyzed or processed in order to identify the border zone is preferably taken after formation of such a steady-state concentration gradient.

Also, prior to reaching steady-state, the formation of the gradient is predictable and can in some cases be directly visualized using, for example, a fluorescent compound, thus enabling a readout of a microorganism response in relation to a known concentration of the test substance already prior to achieving a steady state gradient.

A single image could be taken of the 3D culture matrix in step S21. Alternatively, images of the 3D culture matrix are periodically taken within an interval of, for instance, 0 to 12 hours from connecting the inputs of the fluid channels to the respective fluid flows. In a particular embodiment, the time interval during which images are periodically taken is preferably 0 to 6 hours, or 0 to 4 hours, or 0 to 3 hours, or more preferably 0 to 2 hours or 0 to 1 hour following starting the monitoring by connecting the fluid channels to the respective fluid flows.

In the foregoing, the discussion has mainly been towards determining the response to a single test substance in the fluid device. However, it is also possible to simultaneously determine the response to multiple test substances, determining the response to a mixture of multiple test substances or indeed determining different responses to multiple test substances or mixtures thereof.

In an embodiment, step S2 of FIG. 1 thereby comprises connecting the input of the first fluid channel to a first fluid flow comprising a first test substance at the first concentration and lacking a second test substance or comprising the second test substance at a third concentration. Step S3 then comprises connecting the input of the second fluid channel to a second fluid flow lacking the first test substance or comprising the first test substance at the second concentration (that is lower than the first concentration) and comprising the second test substance at a fourth concentration that is higher than the third concentration. A first concentration gradient of the first test substance and a second concentration gradient of the second test substance are thereby formed over at least a portion of the 3D culture matrix.

Step S4 comprises, in this embodiment, determining a response of the microorganism to the first test substance and the second substance based on respective positions of any border zones in the 3D culture matrix relative to the first and/or second end portion or side of the culture chamber. The border zone is between a first response zone in which the microorganism shows a first response to the first test substance and the second test substance and a respective second response zone in which the microorganism shows a second, different response to the first test substance and the second test substance.

Hence, in this embodiment a concentration gradient of the first test substance is established from the first fluid channel (high concentration of the first test substance) over at least a portion of the 3D culture matrix to the second fluid channel (low concentration of the first test substance). Correspondingly, a concentration gradient of the second test substance is established from the second fluid channel (high concentration of the second test substance) over at least a portion of the 3D culture matrix to the first fluid channel (low concentration of the second test substance).

If the test substances, for example, are different antibiotics it could be possible that two border zones are present. In one case, when travelling from the first fluid channel towards the second fluid channel the 3D culture matrix could be divided among the following zones: a first "death" zone with no viable or growing microorganisms, a first border zone, a growth zone with viable and growing microorganisms, a second border zone and a second "death" zone. The positions and widths (shape) of the respective zones depend on the particular antibiotics, the concentrations of the antibiotics (first and fourth concentrations and optional second and third concentrations) and the particular microorganisms.

In another approach, step S2 comprises connecting the input of the first fluid channel to the first fluid flow comprising a first test substance at the first concentration and comprising a second test substance at a third concentration. Step S3 then comprises connecting the input of the second fluid channel to the second fluid flow lacking the first test substance or comprising the first test substance at the second concentration (that is lower than the first concentration) and lacking the second test substance or comprising the second test substance at a fourth concentration that is lower than the third concentration. A first concentration gradient of the first test substance and a second concentration gradient of the second test substance are thereby formed over at least a portion of the 3D culture matrix.

Step S4 comprises, in this embodiment, determining a response to the microorganism to a mixture of the first and second test substances based on a position of any border zone in the 3D culture matrix relative to the first and/or second end portions or sides of the culture chamber. The border zone is between a first response zone in which the microorganism shows a first response to the mixture and a second response zone in which the microorganism shows a second, different response to the mixture.

Hence, in this embodiment a concentration gradient of the first test substance is established from the first fluid channel (high concentration of the first test substance) over at least a portion of the 3D culture matrix to the second fluid channel (low concentration of the first test substance). Correspondingly, a concentration gradient of the second test substance is established from the first fluid channel (high concentration of the second test substance) over at least a portion of the 3D culture matrix to the second fluid channel (low concentration of the second test substance).

This embodiment differs from the previous one in that the first fluid flow comprises the highest concentration of both test substances whereas in the previous embodiment the first fluid flow had the highest concentration of the first test substance whereas the second fluid flow had the highest concentration of the second test substance.

The present embodiment is thereby more appropriate for determining the response of microorganisms to a mixture or cocktail of test substances. The previous embodiment in clear contrast enables parallel testing of two test substances using a single fluidic device and a single culture chamber.

In an embodiment, the culture chamber of the fluidic device has at least four end portions or sides that can be connected to respective fluid flows. Hence, the culture chamber then additionally has a third fluid channel flanking a third end portion or side of the culture chamber and a fourth channel flanking a fourth, different end portion or side of the culture chamber. In this embodiment, the test substance is a first test substance.

The method then comprises the additional steps of connecting an input of the third fluid channel to a third fluid flow comprising a second test substance at a third concentration and connecting an input of the fourth fluid channel to a fourth fluid flow lacking the second test substance or comprising the second test substance at a fourth concentration that is lower than the third concentration. Hence, a concentration gradient of the second test substance is formed over at least a portion of the 3D culture matrix. In this embodiment, the method also comprises determining a response of the microorganism to the second test substance based on a position, relative to the third and/or fourth end portion or side, of any border zone in the 3D culture matrix. This border zone is between a first response zone in which the microorganism shows a first response to the second test substance and a second response zone in which the microorganism shows a second, different response to the second test substance.

In this embodiment, two test substances can be tested in parallel. For instance, if the culture chamber and the 3D culture matrix has a rectangular or quadratic cross-section then the concentration gradient of the first test substance can be established along the X direction between the first and second fluid channels, whereas the concentration gradient of the second test substance is then established along the Y direction between the third and fourth fluid channels.

Here below, a particular use of the method will be further described with the test substance being an antibiotic or other form of bactericide and/or bacteriostat. In this embodiment, step S4 of FIG. 1 comprises determining susceptibility of the microorganism to the test substance based on a position of the border zone in the 3D culture matrix relative to the first and/or second end portion or side of the culture chamber. This border zone is then between a growth zone of growing microorganism and a non-growth zone lacking growth of the microorganism.

In this embodiment, an additional step as shown in FIG. 5 can be performed. The method continues from step S4 of FIG. 1. The following step S40 determines resistance of the microorganism to the test substance based on a width of the border zone. Hence, if the border zone has a non-zero width then microorganisms that are resistant to the test substance are able to grow in the concentration range corresponding to the border zone. A variant of step S40 comprises determining resistance of the microorganism to the test substance based on a shape of the border zone.

FIG. 6 is a flow diagram illustrating an embodiment of step S4 of FIG. 1 that can be used to determine MIC of the test substance from an image taken of the 3D culture matrix in step S21 of FIG. 3, for instance, using a bright-field or phase-contrast microscope. The method, thus, continues from step S22 in FIG. 3 and continues to step S50. This step S50 comprises determining a relation of the detected light intensity versus position in the 3D culture matrix between the first end portion or side and the second, different end portion or side of the culture chamber. Hence, this step S50 basically corresponds to determining the detected light intensity at different distances between the first end portion or side and the second end portion of the side. This relation could, for instance, be in the form of a graph or plot showing how the detected light intensity versus the distance between the first and second end portions of the culture chamber, see FIGS. 17B and 18B.

For instance, the 3D culture matrix could be regarded as a matrix of rows and columns with detected light intensity values. In such a case, a row could represent the detected light intensity values when travelling from the first side of the 3D culture matrix towards the second, opposite side of the 3D culture matrix in the case of a rectangular or quadratic 3D culture matrix. Such a row is then parallel with the direction of the concentration gradient. In an embodiment, an average row with average detected light intensity values is obtained by summarizing the detected light intensity values of all rows and dividing the respective summed values by the number of rows. Alternatively, a sum row is calculated by summarizing the detected light intensity values of all rows in a direction perpendicular to the direction of the concentration gradient. The determination of the detected light intensity at different distances can then be performed on the average row or the sum row.

A following step S51 then comprises determining a MIC of the test substance for the microorganism based on the relation.

Figure 17B:
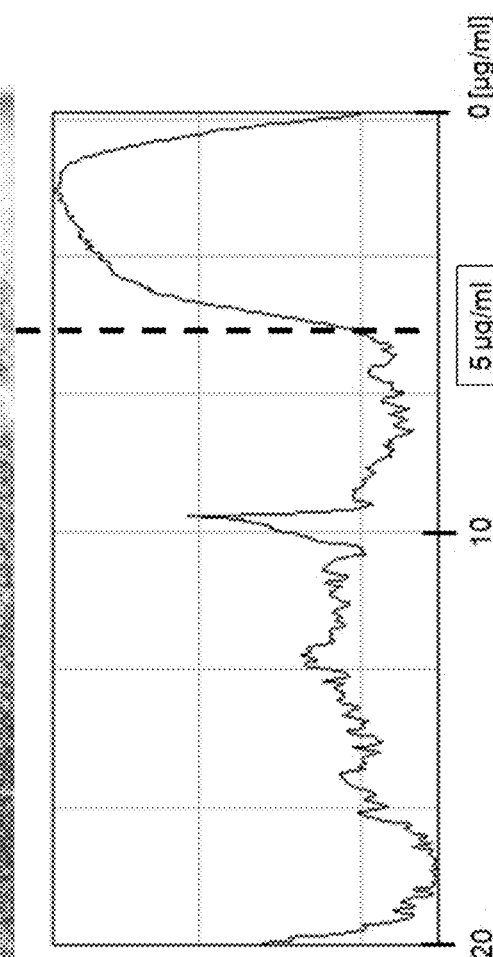
FIG. 17B illustrates an intensity profile of the selected area in FIG. 17A with an intensity increase at 5 µg/ml indicating the minimum inhibitory concentration of *E. coli* K12 MG1655 for ampicillin.

FIG. 7 is a flow diagram illustrating in more detail how this MIC determination can be performed. The method continues from step S50. A next step S60 comprises identifying a position at which there is a kink in a signal representing the relation between detected light intensity and position. This signal could thus be a representation of the graphs as shown in FIGS. 17B and 18B. Step S60, thus, investigates the signal and identifies the position at which there is a kink in the signal.

A next step S61 comprises converting the position identified in step S60 and corresponding to the kink into a concentration of the test substance based on predefined gradient information defining concentration versus position in the 3D culture matrix. Hence, in this approach there is a predefined relation between the concentration of the test substance in the 3D culture matrix and the position relative one of the end portions.

Generally, the concentration gradient is a linear concentration gradient at steady-state, i.e. ranging from the first concentration at the first end portion or side to the second concentration or zero concentration at the second end portion or side. In such a case, there is a simple relation between the concentration of the test substance and the distance or position relative to one of the end positions.

It is also possible to label, such as using a radioactive label, the test substance or use an easily detectable, such as fluorescent, detection substance that has substantially similar diffusion characteristics, mainly dictated by the size of the molecule, through the 3D culture matrix as the test substance. In such a case, the concentration gradient of the radioactively labelled test substance or the detection substance could be easily measured and the predefined gradient information defining concentration versus position in the 3D culture matrix can be determined from such an experiment.

In either case, the predefined gradient information enables converting the position determined in step S60 into a concentration value that corresponds to the MIC of the test substance in step S61.

The time it takes to establish a steady-state gradient within the 3D culture matrix depends on the width of the 3D culture matrix between the two fluid channels and the diffusions constant of the test substance. The diffusion constant is, in turn, dependent on the temperature, the viscosity of the 3D culture matrix and the radius of the molecules of the test substance. For example, ampicillin in agarose matrix has a diffusion constant of $D=0.016$ $cm^2/h$ [18].

FIGS. 9 to 15 illustrate portions of fluidic devices according to different embodiments showing various numbers and positions of fluid channels and different configurations of culture chambers. The shown figures should, however, merely be seen as a few illustrative examples of the embodiments and further variants and modifications are possible and within the scope of the embodiments.

Figure 9:
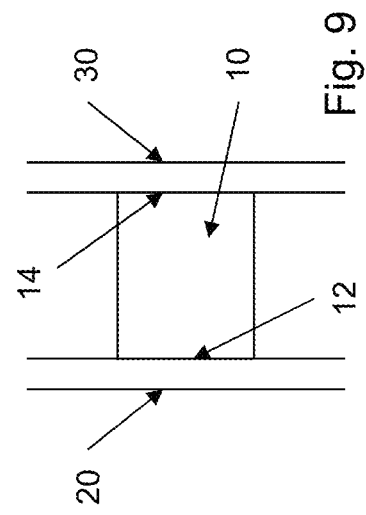
FIG. 9 is a schematic illustration of a culture chamber and fluid channels of a microfluidic device according to an embodiment.

FIG. 9 illustrates an embodiment of a fluidic device with a rectangular or quadratic culture chamber 10 having a first fluid channel 20 flanking a first side 12 and a second fluid channel 30 flanking a second, opposite side 14 of the culture chamber 10. In this embodiment, a linear concentration gradient will be established during steady state over the whole 3D culture matrix present in the culture chamber 10.

Figure 10:
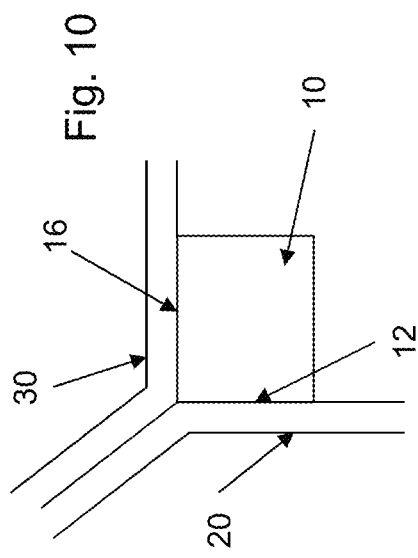
FIG. 10 is a schematic illustration of a culture chamber and fluid channels of a microfluidic device according to another embodiment.

The two fluid channels do not necessarily have to flank opposite sides of the culture chamber as shown in FIG. 9. FIG. 10 illustrates the culture chamber 10 with the first fluid channel 20 and the second fluid channel flanking two adjacent sides 12, 16 of the culture chamber 10. In this embodiment, the concentration gradient will be established between these two adjacent sides 12, 16.

Figure 11:
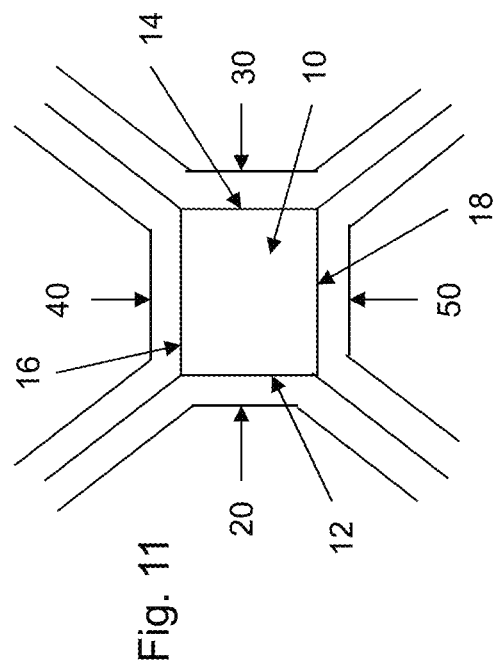
FIG. 11 is a schematic illustration of a culture chamber and fluid channels of a microfluidic device according to a further embodiment.

It is, as has been discussed in the foregoing, possible to use more than two fluid channels. FIG. 11 illustrates an embodiment in which each side 12, 14, 16, 18 of the culture chamber 10 is flanked by a respective fluid channel 20, 30, 40, 50. In this approach two different test substances could be tested in order to establish a first linear concentration gradient of a first test substance over the 3D culture matrix from the first fluid channel 20 to the second, opposite fluid channel 30 (X direction). A second linear concentration gradient of a second test substance over the 3D culture matrix can then be established from the third fluid channel 40 to the fourth, opposite fluid channel 50 (Y direction).

Figure 12:
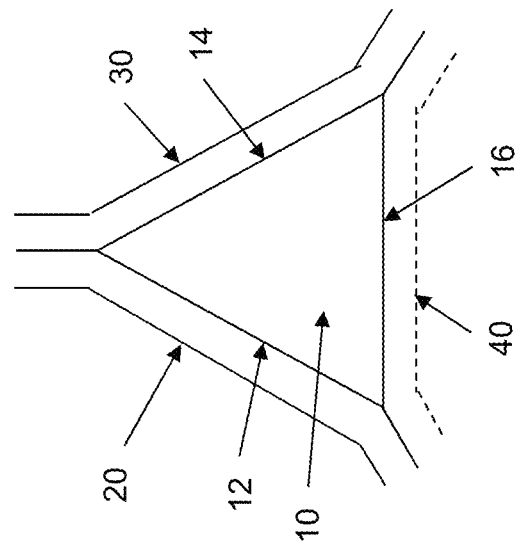
FIG. 12 is a schematic illustration of a culture chamber and fluid channels of a microfluidic device according to yet another embodiment.

In FIGS. 9-11 a rectangular or quadratic culture chamber 10 has been disclosed. The embodiments are however not limited thereto. FIG. 12 illustrates a culture chamber 10 having a triangular configuration with a first fluid channel 20 flanking a first side 12, a second fluid channel 30 flanking a second, adjacent side 14 and optionally also a third fluid channel 40 flanking a third, adjacent side 16 of the culture chamber 10.

Figure 13:
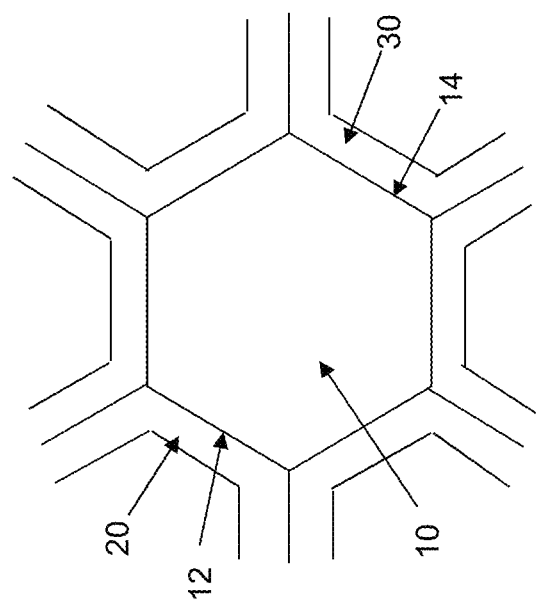
FIG. 13 is a schematic illustration of a culture chamber and fluid channels of a microfluidic device according to a further embodiment.

Also more complex culture chamber configurations with five, six, seven or even more sides are possible. FIG. 13 illustrates a hexagonal culture chamber 10 having six sides 12, 14 and up to six fluid channels 20, 30, of which only two are marked with reference signs in the figure. Hence, in this embodiment it is possible to establish three different linear concentration gradients and thereby testing three different test substances in a single fluidic device.

Figure 14:
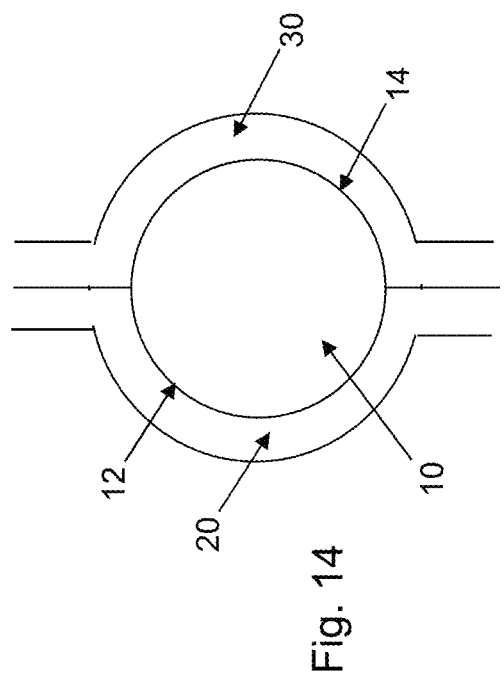
FIG. 14 is a schematic illustration of a culture chamber and fluid channels of a microfluidic device according to still another embodiment.

The fluidic device may also comprise circular or elliptical culture chambers 10 as schematically shown in FIG. 14. In such a case, the fluid channels 20, 30 flank respective end portions 12, 14 of the culture chamber 10. These end portions 12, 14 correspond to different portions of the circumference of the culture chamber 10 and thereby to different portions of the lateral surface of the 3D culture matrix to be arranged in the culture chamber 10.

Figure 15:
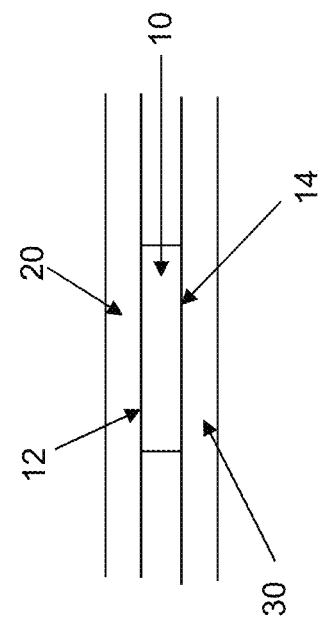
FIG. 15 is a schematic illustration of a culture chamber and fluid channels of a microfluidic device according to yet another embodiment.

In FIGS. 9-14 the fluid channels have been flanking end portions in the form of sides or portions of the circumference of the culture chamber. It is also, or alternatively, possible to have fluid channels 20, 30 flanking end portions 12, 14 in terms of top or upper side or ceiling 12 and bottom or lower side 14 of the culture chamber 10 as shown in FIG. 15.

The present embodiments can be used to determine the identity of and to monitor various microorganisms, test substances and responses. Hence, the embodiments find many different uses within hospital clinics, laboratories, diagnostic laboratories, healthcare facilities, etc.

For instance, the embodiments can be used to identify MIC, or other concentration thresholds that have an effect or no effect, of a bioactive compound in order to identify the minimum concentration of the bioactive compound that has an effect on any given microorganism with regard to growth, proliferation, death or survival of the microorganism.

Furthermore, by establishing MIC for a set of different test substances, the phenotypic identity of a tested microorganism can be established in, for example, a diagnostic test. The analysis of phenotype could result in either full identification of the microorganism strain or result in a general classification of the microorganism with regard to responses to various test substances.

The embodiments can also be used to follow the change of MIC for a test compound on the growth, proliferation, viability or other behavioural aspect of the microorganism over time. This approach enables monitoring of development or loss of resistance, such as antibiotic resistance, in the microorganism over time through several generations, thereby altering the ability of the microorganism to metabolize or resist the effects of the test substance. This type of experiment can be used to provide an indication of suitable clinical dose of the test substance and/or frequency of administration. Hence, the embodiments can be used to study both the pharmacodynamics and the pharmacokinetics of any test substance or combination of test substances in any given type of microorganism.

The embodiments can further be used to evaluate and identify combinations of test substances, such as antibiotics, which together are more efficient than the individual substances, or to evaluate if the test substances have synergistic effect, or if they together have no effects on, for example, the growth, proliferation, viability or other behavioural aspect of the microorganism.

The embodiments can be used to screen novel drugs or chemical compounds for their effects on microorganism growth, proliferation, viability, death, ability to spread, or other behavioural aspects of the microorganism.

The embodiments can also be used to quickly get a first profile of response of any given microorganism to substances used in clinical practice. The aim could then be to identify substances that are suitable for anti-microorganism treatment of patients suffering from microbial infections. This can be used even in cases where the life of the patient depends on a fast identification of the microorganism causing the infection in order to design an appropriate treatment.

The embodiments can further be used to study the effects of drugs or test substances on host cells that have been infected with viruses, with effects on cell behaviour, cell survival, cell proliferation, cell death and/or cell differentiation used as readouts for the amount and effect of the viruses and test substances on the host cells. In this application, the viruses are preferably placed together with the cells that they are known to be able to infect. Thus, both direct effects on the virus particles as well as on the infected host cells, such as cytopathic effects, can be used to study the effects of test substances at different concentrations.

As an example of the study of the effects of drugs on parasites, Malaria parasites could be studied using human or mouse red blood cells infected with the parasite and cultured in the 3D culture matrix of the fluidic device. The response of the parasites and red blood cells to one or more gradients of drug(s) can then be tested.

Culturing microorganisms in a 3D culture matrix in a culture chamber of a fluidic device enables keeping the microorganisms inside an at least partly closed culture chamber. This provides protection for the personnel against potentially harmful microorganisms but also protects against contamination of the test sample in the 3D culture matrix.

Figure 16:
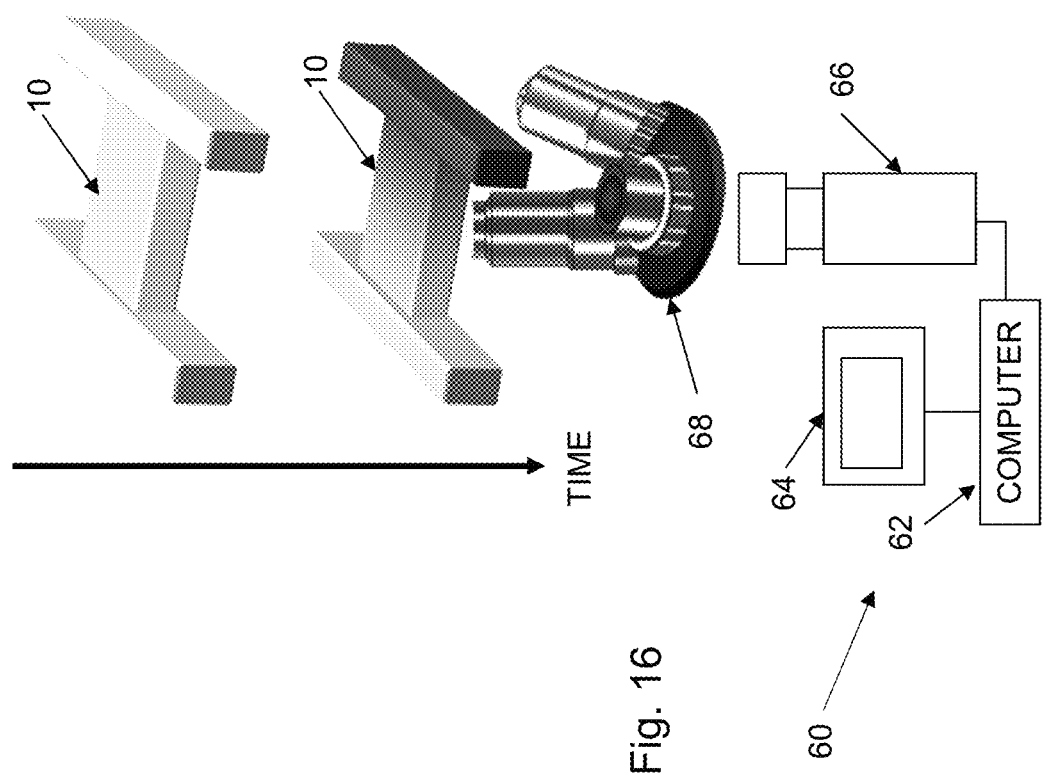
FIG. 16 schematically illustrates a system for determining a response of a microorganism to a test substance according to an embodiment together with a time series showing formation of a concentration gradient in the 3D culture matrix.

Another aspect of the embodiments relates, see FIG. 16, to a system 60 for determining a response of a microorganism to a test substance. The system 60 comprises a fluidic device represented by the culture chamber 10 and flanking channels in the figure. The fluidic device comprises a culture chamber 10 configured to house a culture of the microorganism in a 3D culture matrix. The fluidic device also comprises a first fluid channel flanking a first end portion or side of the culture chamber 10 and a second fluid channel flanking a second, different end portion or side of the culture chamber 10. The system 60 further comprises a first fluid reservoir (see FIG. 8) comprising a first fluid comprising the test substance at a first concentration. The first fluid reservoir is configured to be connected to an input of the first fluid channel. The system 60 also comprises a second fluid reservoir comprising a second fluid lacking the test substance or comprising the test substance at a second concentration that is lower than the first concentration. The second fluid reservoir is configured to be connected to an input of the second fluid channel to form a concentration gradient of the test substance over at least a portion of the 3D culture matrix.

The system 60 also comprises a computer-based system 62, 66 configured to take at least one image of the 3D culture matrix and process the at least one image to identify a position, relative to the first end portion and/or second, different end portion, of any border zone in the 3D culture matrix. This border zone is between a first response zone in which the microorganism shows a first response to the test substance and a second response zone in which the microorganism shows a second, different response to the test substance. The computer-based system 62, 66 is also configured to determine a response of the microorganism to the test substance based on the position of the border zone.

In FIG. 16 the computer-based system 62, 66 has been exemplified by a camera or other image or signal capturing equipment or detector 66. This camera or detector 66 is preferably, but not necessarily, connected to or arranged in relation to a microscope 68 as shown in the figure in order to take the picture of the 3D culture matrix. The camera 66 is preferably connected to a computer 62 comprising a memory configured to store the image data and a computer program comprising code means to be executed by a processing unit of the computer 62. The computer program is then configured to identify the position and optionally the width and/or shape of the border zone in the image, such as based on detected light intensity or detected fluorescence. The computer program is preferably also configured to convert the position of the border zone into a concentration value or a range of concentration values for the test substance as previously disclosed herein.

An optional screen 64 of the system 60 can be connected to the computer 62 in order to display the captured image (FIG. 17A or 18A), a processed graph showing detected light intensity or detected fluorescence versus position in the 3D culture matrix or versus concentration of the test substance along the concentration gradient (FIG. 17B or 18B), and/or the determine concentration or concentration range.

Another aspect of the embodiments relates to use of a fluidic device to determine a response of a microorganism to a test substance. The fluidic device comprises a culture chamber configured to a house a culture of the microorganism in a 3D culture matrix. The fluidic device also comprises a first fluid channel flanking a first end portion of the culture chamber and configured to carry a first fluid flow comprising the test substance at a first concentration. The fluidic device further comprises a second fluid channel flanking a second, different end portion of the culture chamber and configured to carry a second fluid lacking the test substance or comprising the test substance at a second concentration that is lower than the first concentration to form a concentration gradient of the test substance over at least a portion of the 3D culture matrix. The use comprises determining the response of the microorganism to the test substance based on a position of any border zone in the 3D culture matrix relative to the first end portion and/or the second, different end portion. The border zone is between a first response zone in which the microorganism shows a first response to the test substance and a second response zone in which the microorganism shows a second, different response to the test substance.

EXPERIMENTS

Experiment 1—Ampicillin

Bacterium strain *E. coli* K12 MG1655 was cultured on a Luria broth (LB) plate. The *E. coli* cells were diluted by phosphate buffered saline (PBS) to $OD_{600}$=0.1 as measured by a MULTISKAN® FC Microplate Photometer (Thermo Scientific). Same volumes of PBS with $OD_{600}$=0.1 cells and low-melting temperature agarose were mixed together. A pipette with white tips was used to suck up 8 µl of the mixture and inject the mixture into the culture chamber of a microfluidic device CELLDIRECTOR® Ruby (Gradientech AB), see upper panel in FIG. 20. The fluid channel inputs of the microfluidic device were connected to fluid reservoirs comprising Muelle-Hinton medium and where one of the reservoirs also contained 20 µg/ml ampicillin. The speed of a pusher used to draw the medium into the fluid channels was set to 5 µl/min for 30 minutes and then to 2 µl/min for the rest of the time.

The microfluidic device was put on an Eclipse TE2000 Nikon inverted microscope system connected to a charged coupled device (CCD) camera. The microfluidic device was connected to a thermal stat to maintain the temperature in the 3D culture matrix at 37° C. during the experiment. In the present experiments the 2× objective lens was used so that the whole culture chamber was in the field of vision of the microscope. Following brightness and focal distance adjustment time-lapse photography of a CCD camera supported software (1 picture/30 s) was turned on.

The pictures were cut to match a selected central portion of the culture chamber, see black box in FIGS. 17A and 18A. Image processing software was used to extract detected light intensity data from the pictures. A spatial growth situation distribution diagram was used to summarize the grey-scale values, i.e. detected light intensity values, of all the lines that are perpendicular to the direction of the gradient as the Y-axis with the concentration gradient as the X-axis.

A significant point, representing MIC of the ampicillin, can be found in this chart. A diagram of the cell growth rate, represented by optical intensity, was also drawn as shown in FIG. 17B.

Figure 17C:
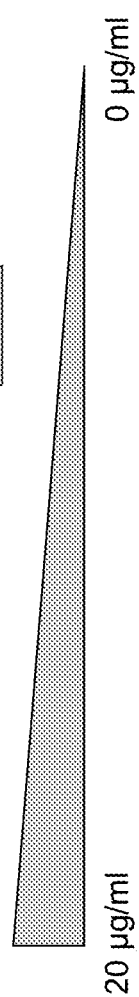
FIG. 17C schematically illustrates the linear gradient of ampicillin (20-0 µg/ml) through the 3D culture matrix of FIG. 17A.

FIG. 17A illustrates the significant cell growth close to the sink fluid channel where concentration of ampicillin is low. The *E. coli* cells correspond to the white band seen in the figure. FIG. 17B illustrates the cell growth versus the concentration gradient of the ampicillin. The MIC was determined to be 5 µg/ml in this experiment. FIG. 17C illustrates the concentration gradient of ampicillin formed in the 3D culture matrix.

Please note that the top seen around 10 µg/ml in FIG. 17B is due to a tear in the 3D culture matrix.

Experiment 2—Spectinomycin

This experiment was performed as in Experiment 1 with the exception that 50 µg/ml spectinomycin was added to one of the fluid reservoirs instead of ampicillin. The results are shown in FIGS. 18A-18C.

FIGS. 18A and 18B clearly demonstrate a much wider border as compared to Experiment 1 (FIGS. 17A and 17B). Hence, this experiment indicated the presence of spectinomycin resistance among the *E. coli* cells, whereas no corresponding ampicillin resistance was detected in Experiment 1.

Figure 19:
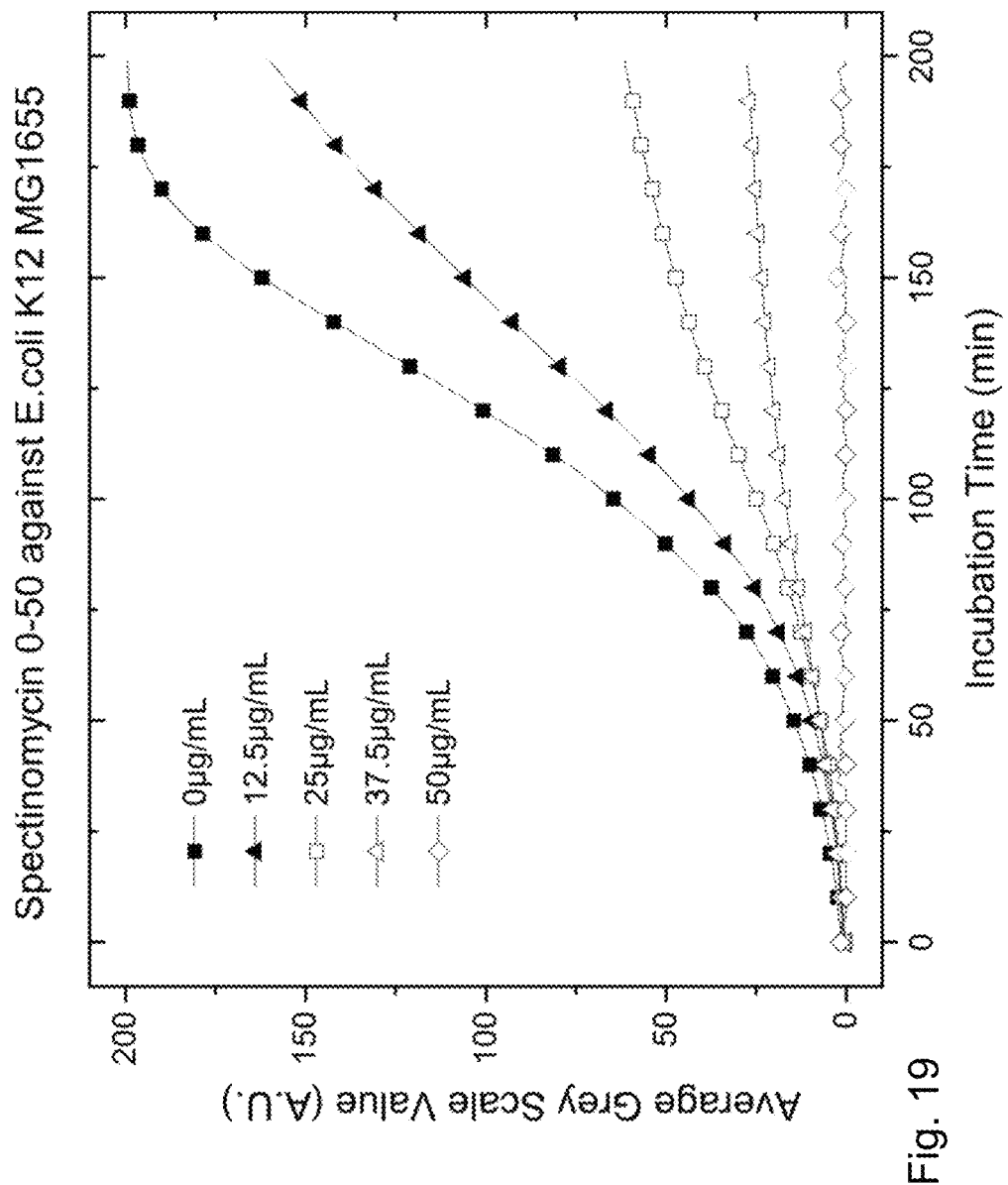
FIG. 19 is a diagram showing growth curves over time for *E. coli* K12 MG1655 exposed to various concentrations of spectinomycin.

FIG. 19 illustrates the average grey scale value, i.e. detected intensity and thereby cell density, at different positions in the 3D culture matrix over time. These different positions correspond to concentrations of 0, 12.5, 25, 37.5 and 50 µg/ml spectinomycin.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

REFERENCES

[1] Boedicker et al., *Lab on a Chip*, 2008, 8: 1265-1272
[2] Churski et al., *Lab on a Chip*, 2012, 12: 1629-1637
[3] Eun et al., *ACS Chemical Biology*, 2010, 6: 260-266
[4] Chen et al., *Analytical Chemistry*, 2010, 82: 1012-1019
[5] Peitz and van Leeuwen, *Lab on a Chip*, 2010, 10: 2944-2951
[6] Chung et al., *Biomicroluidics*, 2011, 5: 021102
[7] Cira et al., *Lab on a Chip*, 2012, 12: 1052-1059
[8] Kalashnikow et al., *Lab on a Chip*, 2012, 12: 4523-4532
[9] Kinnunen et al., *Small*, 2012, 8: 2477-2482
[10] Choi et al., *Lab on a Chip*, 2013, 13: 280-287
[11] Kim et al., *Lab on a Chip*, 2010, 10: 3296-3299
[12] Haessler et al., *Biomed Microdevices*, 2009, 11: 827-835
[13] Kim et al., *Lab on a Chip*, 2012, 12: 2255-2264
[14] Nguyen et al., *PNAS*, 2013, 110: 6712-6717
[15] Frisk et al., *Electrophoresis*, 2007, 28: 4705-4712
[16] WO 2010/056186
[17] WO 2012/033439
[18] Humphrejy et al., *J Gen Mircrobiol*, 1952, 7: 29-143
[19] Hou et al., *Lab on a Chip*, 2014, Accepted manuscript, DOI: 10.1039/C4LC00451E

The invention claimed is:

1. A system for determining a response of a microorganism to a test substance, the system comprising:
    a fluidic device comprising:
        a culture chamber configured to house a culture of the microorganism in a three dimensional (3D) culture matrix;
        a first fluid channel flanking a first end portion of the culture chamber; and
        a second fluid channel flanking a second, different end portion of the culture chamber;
    a first fluid reservoir comprising a first fluid comprising the test substance at a first concentration, the first fluid reservoir is configured to be connected to an input of the first fluid channel;
    a second fluid reservoir comprising a second fluid lacking the test substance or comprising the test substance at a second concentration that is lower than the first concentration, the second fluid reservoir is configured to be connected to an input of the second fluid channel to form a concentration gradient of the test substance over at least a portion of the 3D culture matrix; and
    a computer-based system configured to i) take at least one image of the 3D culture matrix, ii) process the at least one image to identify a position, relative to the first end portion and/or the second, different end portion, of any border zone in the 3D culture matrix between a growth zone of growing microorganism and a non-growth zone lacking growth of the microorganism, wherein the growth of the microorganism in the growth zone is not inhibited by the test substance, iii) process the at least one image to identify a width of the any border zone, iv) determine a minimal inhibitory concentration (MIC) of the microorganism to the test substance based on the position of the any border zone by correlating the position to a concentration or a concentration range of the test substance based on gradient information defining concentration versus position in the 3D culture matrix for the concentration gradient, and v) determine a resistance of the microorganism to the test substance based on the width of the any border zone.

2. The system according to claim 1, further comprising at least one pump configured to pump the first fluid from the first fluid reservoir into the input of the first fluid channel and out through an output of the first fluid channel and pump the second fluid from the second fluid reservoir into the input of the second fluid channel and out through an output of the second fluid channel.

3. The system according to claim 1, wherein the computer-based system is configured to take the at least one image of the 3D culture matrix at least after formation of a steady-state concentration gradient of the test substance over the at least a portion of the 3D culture matrix.

4. The system according to claim 1, wherein
the test substance is a first test substance and the concentration gradient is a first concentration gradient;
the first fluid reservoir comprises the first fluid i) comprising the first test substance at the first concentration, and ii) lacking a second test substance or comprising the second test substance at a third concentration;
the second fluid reservoir comprises the second fluid i) lacking the first test substance or comprising the first test substance at the second concentration, and ii) comprising the second test substance at a fourth concentration that is higher than the third concentration to form the first concentration gradient of the first test substance and a second concentration gradient of the second test substance over the at least a portion of the 3D culture matrix;
the computer-based system is configured to ii) process the at least one image to identify respective positions, relative to the first end portion and/or the second, different end portion, of any one or more border zones in the 3D culture matrix between a growth zone of growing microorganism and a respective non-growth zone lacking growth of the microorganism, wherein the growth of the microorganism in the growth zone is not inhibited by the first test substance or the second test substance, iii) process the at least one image to identify respective widths of the any one or more border zones, iv) determine a MIC of the microorganism to the first test substance and the second test substance based on the respective positions of the any one or more border zones by correlating the respective positions to a concentration or a concentration range of the respective test substance based on gradient information defining concentration versus position in the 3D culture matrix for the respective concentration gradient, and v) determine the resistance of the microorganism to the first test substance and the second test substance based on the respective widths of the any one or more border zones.

5. The system according to claim 1, wherein
the test substance is a first test substance and the concentration gradient is a first concentration gradient;
the first fluid reservoir comprises the first fluid i) comprising the first test substance at the first concentration, and ii) comprising a second test substance at a third concentration;
the second fluid reservoir comprises the second fluid i) lacking the first test substance or comprising the first test substance at the second concentration, and ii) lacking the second test substance or comprising the second test substance at a fourth concentration that is lower than the third concentration to form the first concentration gradient of the first test substance and a second concentration gradient of the second test substance over the at least a portion of the 3D culture matrix;
the computer-based system is configured to ii) process the at least one image to identify respective positions, relative to the first end portion and/or the second, different end portion, of any one or more border zones in the 3D culture matrix between a growth zone of growing microorganism and a respective non-growth zone lacking growth of the microorganism, wherein growth of the microorganism in the growth zone is not inhibited by the first test substance or the second test substance, iii) process the at least one image to identify respective widths of the any one or more border zones, iv) determine a MIC of the microorganism to the first test substance and the second test substance based on the respective positions of the any one or more border zones by correlating the respective position to a concentration or a concentration range of the respective test substance based on gradient information defining concentration versus position in the 3D culture matrix for the respective concentration gradient, and v) determine the resistance of the microorganism to the first test substance and the second test substance based on the respective widths of the any one or more border zones.

6. The system according to claim 1, wherein
the test substance is a first test substance, the concentration gradient is a first concentration gradient, the growth zone is a first growth zone and the non-growth zone is a first non-growth zone;
the fluidic device comprises:
a third fluid channel flanking a third end portion of the culture chamber; and
a fourth fluid channel flanking a fourth, different end portion of the culture chamber;
a third fluid reservoir comprising a third fluid comprising a second test substance at a third concentration, the third fluid reservoir is configured to be connected to an input of the third fluid channel;
a fourth fluid reservoir comprising a fourth fluid lacking the second test substance or comprising the second test substance at a fourth concentration that is lower than the third concentration, the fourth fluid reservoir is configured to be connected to an input of the fourth fluid channel to form a second concentration gradient of the second test substance over at least a portion of the 3D culture matrix; and
the computer-based system configured to ii) process the at least one image to identify a second position, relative to third first end portion and/or the fourth, different end portion, of any additional border zone in the 3D culture matrix between a second growth zone of growing microorganism and a second non-growth zone lacking growth of the microorganism, wherein growth of the microorganism in the second growth zone is not inhibited by the second test substance, iii) process the at least one image to identify a second width of the any additional border zone, iv) determine a MIC of the microorganism to the second test substance based on the second position of the any additional border zone by correlating the second position to a concentration or a concentration range of the second test substance based on gradient information defining concentration versus position in the 3D culture matrix for the second concentration gradient, and v) determine a resistance of the microorganism to the second test substance based on the second width of the any additional border zone.

7. The system according to claim 1, wherein the computer-based system is configured to detect light intensity in the at least one image, and identify the any border zone in the 3D culture matrix based on the detected light intensity.

* * * * *